United States Patent
Jacobson

(10) Patent No.: US 10,869,835 B2
(45) Date of Patent: *Dec. 22, 2020

(54) FORMULATIONS AND METHODS FOR LYOPHILIZATION AND LYOPHILATES PROVIDED THEREBY

(71) Applicant: BIOGEN CHESAPEAKE LLC, Cambridge, MA (US)

(72) Inventor: Sven Martin Jacobson, New York, NY (US)

(73) Assignee: Biogen Chesapeake LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/585,255

(22) Filed: Sep. 27, 2019

(65) Prior Publication Data

US 2020/0093747 A1 Mar. 26, 2020

Related U.S. Application Data

(63) Continuation of application No. 16/138,173, filed on Sep. 21, 2018, now Pat. No. 10,426,729, which is a continuation of application No. 14/508,488, filed on Oct. 7, 2014, now Pat. No. 10,117,834, which is a continuation of application No. 13/610,335, filed on Sep. 11, 2012, now Pat. No. 8,858,997, which is a continuation of application No. 12/746,164, filed as application No. PCT/US2008/085384 on Dec. 3, 2008, now Pat. No. 8,277,845.

(60) Provisional application No. 60/992,241, filed on Dec. 4, 2007.

(51) Int. Cl.
| | |
|---|---|
| A61K 9/19 | (2006.01) |
| A61K 9/16 | (2006.01) |
| A61K 9/00 | (2006.01) |
| A61K 31/175 | (2006.01) |
| A61K 31/451 | (2006.01) |
| A61K 31/64 | (2006.01) |

(52) U.S. Cl.
CPC .......... *A61K 9/1682* (2013.01); *A61K 9/0019* (2013.01); *A61K 9/1611* (2013.01); *A61K 9/1623* (2013.01); *A61K 9/19* (2013.01); *A61K 31/175* (2013.01); *A61K 31/451* (2013.01); *A61K 31/64* (2013.01); *Y10S 514/96* (2013.01)

(58) Field of Classification Search
CPC ...................................................... A61K 9/19
See application file for complete search history.

(56) References Cited

U.S. PATENT DOCUMENTS

| | | | |
|---|---|---|---|
| 4,384,975 A | 5/1983 | Fong et al. | |
| 5,258,185 A | 11/1993 | Bauer et al. | |
| 5,354,562 A | 10/1994 | Platz et al. | |
| 5,747,002 A | 5/1998 | Clark et al. | |
| 5,817,343 A | 10/1998 | Burke | |
| 5,856,360 A | 1/1999 | Salzman et al. | |
| 5,859,037 A | 1/1999 | Whitcomb | |
| 5,952,008 A | 9/1999 | Backstrom et al. | |
| 5,977,109 A | 11/1999 | Nakakura et al. | |
| 6,537,578 B1 | 3/2003 | Bhagwat et al. | |
| 7,285,574 B2 | 10/2007 | Simard et al. | |
| 8,277,845 B2 * | 10/2012 | Jacobson | A61K 31/64 424/484 |
| 8,858,997 B2 * | 10/2014 | Jacobson | A61K 9/1682 424/484 |
| 10,117,834 B2 * | 11/2018 | Jacobson | A61K 31/64 |
| 10,426,729 B2 * | 10/2019 | Jacobson | A61K 9/1623 |
| 2002/0022738 A1 | 2/2002 | Takada et al. | |
| 2003/0125338 A1 | 7/2003 | Connop | |
| 2003/0215889 A1 | 11/2003 | Simard | |
| 2006/0100183 A1 | 5/2006 | Simard | |
| 2006/0115539 A1 | 6/2006 | Prasch | |
| 2006/0183803 A1 | 8/2006 | Hevia et al. | |
| 2006/0189663 A1 | 8/2006 | Holm | |
| 2006/0276411 A1 | 12/2006 | Simard | |
| 2007/0015687 A1 | 1/2007 | Szillvassy | |
| 2007/0249583 A1 | 10/2007 | Stein | |
| 2008/0220441 A1 | 9/2008 | Birnbaum | |
| 2009/0233995 A1 | 9/2009 | Lautt | |

FOREIGN PATENT DOCUMENTS

| | | |
|---|---|---|
| EP | 0362704 A1 | 4/1990 |
| JP | H2149516 A | 6/1990 |

(Continued)

OTHER PUBLICATIONS

Galal, et al., "Formation of fast release glibenclamide liquid and semi-solid matrix filled capsules", Acta Phann, 53: pp. 57-64, (2003).

(Continued)

*Primary Examiner* — Svetlana M Ivanova

(74) *Attorney, Agent, or Firm* — Rothwell, Figg, Ernst & Manbeck, P.C.

(57) ABSTRACT

The present invention provides compositions, methods for lyophilizing compounds and making pharmaceutical compositions, and kits providing solutions and lyophilized formulations of compounds. The compositions, methods, and kits are particularly useful in pharmaceutical applications involving therapeutic agents that have low solubility at low and medium pH values. Certain embodiments provide methods for lyophilizing compounds in liquid solutions, which include the steps of: a) preparing aqueous solutions of a compound of interest in the absence of buffer; b) adjusting the pH to high values of pH in order to increase the solubility of the compound of interest; and c) freeze-drying the solution to provide a lyophilized solid composition. Aqueous solutions including buffer are also disclosed. Lyophilized formulations, including micronized and non-micronized powders, are provided.

23 Claims, 8 Drawing Sheets

(56) References Cited

FOREIGN PATENT DOCUMENTS

| | | |
|---|---|---|
| JP | 05004917 | 1/1993 |
| JP | A-H5-4917 | 2/1994 |
| JP | 2002080361 A | 3/2002 |
| JP | 2006527223 A | 11/2006 |
| JP | 2007504258 | 3/2007 |
| WO | 97/41857 A1 | 11/1997 |
| WO | 98/36755 | 8/1998 |
| WO | 199906024 A1 | 2/1999 |
| WO | 2002079778 A2 | 10/2002 |
| WO | 2003063825 A1 | 8/2003 |
| WO | 2005023223 | 3/2005 |
| WO | 2008038126 A2 | 4/2008 |
| WO | 2009073711 A1 | 11/2009 |

OTHER PUBLICATIONS

Stefani, et al., "Intra-septal injections of glucose and glibenclamide attenuate galanin-induced spontaneous alternation performance deficits in the rat", Brain Research 813: pp. 50-56, (1998).

Chen, et al., "Cell swelling and a nonselective cation channel regulated by internal Ca2+ and ATP in native reactive astrocytes from adult rat brain", The Journal of Neuroscience, 21(17): 6512-6521, (2001).

Chen, et al., "Functional coupling between sulfonylurea receptor type 1 and a nonselective cation channel in reactive astrocytes from adult rat brain", The Journal of Neuroscience, 23(24): 8568-8577, (2003).

Gold, et al., "Intra-septal injections of glucose and glibenclamide attenuate galanin-induced spontaneous alternation performance deficits in the rat", Brain Research, 813: 50-56, ( 1998).

Junquero, et al., "Pharmacological profile of F 12511, (S)-2', 3', 5'-trimethyl-4'-hydroxy-a-dodecylthioacetanilide a powerful and systemic acylcoenzyme A: cholesterol acyltransferase inhibitor", Biochemical Pharmacology, 61: 97-108, (2001).

Sano, et al., "Preventing Alzheimer's disease: Separating fact from fiction", CNS Drugs, vol. 22, pp. 887-902, (2008).

Simard, et al., "Non-selective cation channels, transient receptor potential channels and ischemic stroke", Biochimica et Biophysica Acta, 1772: 947-957, (2007).

Tanaka, et al., "Inhibitors of Acyl-CoA: Cholesterol 0-Acyltransferase. 2. Identification and structure—Activity relationships of a novel series of N-Alk 1-N-(heteroaryl-substituted benzyl)-N-arylureas", J. Med. Chem., 41: 2390-2410, (1998).

Vanelli, et al., "Cardiovascular responses to glibenclamide during endotoxaemia in the pig", Veterinary Research Communications, 21: 187-200, (1997).

Avdeef, et al.; Pharmaceutical Research, Mar. 2007, vol. 24, No. 3, pp. 530-545;"Solubility Excipient classification Gradient Maps"; 16 pages.

Betageri, et al.; "Enhancement of Dissolution of glyburide by solid dispersion and lyophilization techniques"; International Journal of Pharmaceutics, vol. 126 (1995) pp. 155-160.

Sharma; et al.; "Development of Dissolution Media for a Poorly Water-Soluble Anti-Diabetic Drig-Glibenclamide"; Int. J. Chem. Science 5(3), 2007; 1457-1462.

Iga, et al.; "Effect of Buffer Species, pH and Buffer Strength on Drug Dissolution Rate and Solubility of Poorly-soluble Acidic Drugs: Experimental and Theoretical Analysis;" Journal of the Takeda Research Laboratories, 1996, vol. 55, pp. 173-187.

El-Massik, et al. "Development of a dissolution medium for glibenclamide", International Journal of Pharmaceutics; 1996, vol. 140, No. 1, pp. 69-76.

Serajuddin; et al.; "Common ion effect on solubility and dissolution rate of the sodium salt of an organic acid"; Journal of Pharmacy and Pharmacology, 1987, vol. 39, No. 8, pp. 587-591.

Gardiner, et al., "Regional haemodynamic responses to infusion oflipopolysaccharide in conscious rats: effects of pre- or post-treatment with glibenclamide", British Journal of Pharmacology, 128: 1772-1778, (1999).

Jennings, "Lyophilization—Introduction and Basic Principles" 1999, pp. 664, CRC Press LLC, Florida.

Glomme et al, "Comparison of a miniaturized shake-flask solubility method with automated potentiometric acid/base titrations and calculated solubilities", J Pharm Sci, 2005, pp. 1-16, vol. 94, Issue 1.

Kaiser, et al., "A review of Glibenclamide Metabolism in Man and Laboratory Animals," Physical and Analytical Chemistry Research, 1975, the UpJohn Company, 31-43.

Mu-Huo et al., Glibenclamide Pretreatment Attenuates Acute Lung Injury by Inhibiting the Inflammatory Responses and Oxidative Stress in a Polymicrobial Sepsis Animal Model, Anes th Perioper Med 2014; 1 ( 1): 36-43.

Pompermayer et al., The ATP-sensitive potassium channel blocker glibenclamide prevents renal ischemia/reperfusion injury in rats, Kidney International, vol. 67 (2005), pp. 1785-1796.

Rydberg et al, "Hypoglycemic activity of glibenclamide (Glibenclamide) metabolites in humans", Diabetes Care,1994, pp. 1026-1030, vol. 17, Issue 9.

Schrage et al, "Effects of combined inhibition of ATP-sensitive potassium channels, nitric oxide, and prostaglandins on hyperemia during moderate exercise", J Appl Physiol. 2006, pp. 1506-1512, vol. 100, Issue 5.

Verges et al., Consensus statement on the care of the hyperglycaemic/ diabetic patient during and in the immediate follow-up of acute coronary syndrome, Diabetes & Metabolism 38 (2012) 113-127.

Kurland et al., Glibenclamide for the Treatment of Acute CNS Injury, Pharmaceuticals 2013, 6, 1287-1303.

Luzi et al., Glibenclamide: an old drug with a novel mechanism of action?, Acta Diabetol (1997) 34: 239-244.

* cited by examiner

| Timepoint/ Conditions | Appearance Before Reconstitution | Appearance After Reconstitution | Reconstitution Time | pH (after reconstitution) | Assay for Glibenclamide | Assay for Related Substances at 230 nm | | | | Water Content | Appearance 24 hr After Reconstitution |
|---|---|---|---|---|---|---|---|---|---|---|---|
| Initial | Clear 20 mL glass vial with a grey stopper and blue flip off seal containing a white to off white cake, approximately 14mm in depth. Slight cracks on surface. | Clear colourless solution free from visible contamination and particulate matter when compared against water for injection contained in a similar vial. | Mean = 30 seconds | Rep 1 = 10.470 Rep 2 = 10.466 Mean pH = 10.47 | Rep 1 = 0.829 mg/mL Rep 2 = 0.821 mg/mL Mean = 0.83 mg/mL | Rep / 1 / 2 Total Area % = 0.12% Area | RRT 0.19 / 0.12 / 0.12 | RRT 0.41 / tr / tr | | Rep 1 = 1.7 mg/vial Rep 2 = 1.6 mg/vial Mean = 1.7 mg/vial | Clear colourless solution containing several small fibres. Fibres not believed to be drug related |
| 6 weeks at 2-8°C | Clear 20 mL glass vial with a grey stopper and blue flip off seal containing an off white cake, approximately 13mm in depth. Slight cracks on surface. | Clear colourless solution free from visible particles and fibres. | Mean = 1 minute | Rep 1 = 10.511 Rep 2 = 10.513 Mean pH = 10.51 | Rep 1 = 0.837 mg/mL Rep 2 = 0.804 mg/mL Mean = 0.82 mg/mL | Rep | RRT 0.19 | RRT 0.331 | RRT 0.41 | Rep 1 = 2.2 mg/vial Rep 2 = 1.8 mg/vial Mean = 2.0 mg/vial | Clear colourless solution containing several small fibres. Fibres not believed to be drug related |

FIG. 4

| Timepoint/ Conditions | Appearance Before Reconstitution | Appearance After Reconstitution | Reconstitution Time | pH (after reconstitution) | Assay for Glibenclamide | Assay for Related Substances at 230 nm | | | | Water Content | Appearance 24 hr After Reconstitution |
|---|---|---|---|---|---|---|---|---|---|---|---|
| 6 weeks at 35°C/60%RH | Clear 20 mL glass vial with a grey stopper and blue flip off seal containing a white to off white cake, approximately 13mm in depth. Slight cracks on surface. | Clear colourless solution free from visible particles. One vial contained one small fibre. | Mean = 30 seconds | Rep 1 = 10.611 Rep 2 = 10.640 Mean pH = 10.63 | Rep 1 = 0.832mg/mL Rep 2 = 0.789mg/mL Mean = 0.81 mg/mL | Rep | RRT 0.19 | RRT 0.33 | RRT 0.41 | Rep 1 = 1.7 mg/vial Rep 2 = 1.7 mg/vial Mean = 1.7 mg/vial | Clear colourless solution containing several small fibres but no visible particulates. Fibres not believed to be drug related |
| | | | | | | 1 | 0.12 | tr | tr | | |
| | | | | | | 2 | 0.12 | nd | tr | | |
| | | | | | | Total Area % = 0.13% Area | | | | | |
| 6 weeks at 40°C/75%RH | Clear 20 mL glass vial with a grey stopper and blue flip off seal containing an off white cake, approximately 13mm in depth. Slight cracks on surface. | Clear colourless solution free from visible particles and fibres. | Rep 1 = 30secs Rep 2 = not recorded | Rep 1 = 10.576 Rep 2 = not reported | Rep 1 = 0.782mg/mL Rep 2 = 0.760mg/mL Mean = 0.77 mg/mL | Rep | RRT 0.19 | RRT 0.33 | RRT 0.41 | Rep 1 = 1.5 mg/vial Rep 2 = 1.5 mg/vial Mean = 1.5 mg/vial | Clear colourless solution containing several small fibres but no visible particulates. Fibres not believed to be drug related |
| | | | | | | 1 | 0.16 | nd | tr | | |
| | | | | | | 2 | 0.16 | nd | tr | | |
| | | | | | | Total Area % = 0.12% Area | | | | | |

FIG. 5

| Timepoint/ Conditions | Appearance Before Reconstitution | Appearance After Reconstitution | Reconstitution Time | pH (after reconstitution) | Assay for Glibenclamide | Assay for Related Substances at 230 nm | Water Content | Appearance 24 hr After Reconstitution |
|---|---|---|---|---|---|---|---|---|
| 6 weeks and 13 days at 35°C/60%RH | Clear 20 mL glass vial with a grey stopper and blue flip off seal containing an off white cake, approximately 12.5mm in depth. Slight cracks on surface. | Clear colourless solution free from visible particles and fibres. | Mean = 30 seconds | Not tested | Not tested | Not tested | Not tested | Clear colourless solution free from visible particles and fibres. |
| 6 weeks and 13 days at 40°C/75%RH | Clear 20 mL glass vial with a grey stopper and blue flip off seal containing an off white cake, approximately 12mm in depth. Slight cracks on surface. | Clear colourless solution free from visible particles and fibres. | Mean = 30 seconds | Rep 1 = 10.338 Rep 2 = 10.433 | Not tested | Not tested | Not tested | Clear colourless solution containing several small fibres but no visible particulates. Fibres not believed to be drug related |

FIG. 6

| Timepoint/ Conditions | Appearance Before Reconstitution | Appearance After Reconstitution | Reconstitution Time | pH (after reconstitution) | Assay for Glibenclamide | Assay for Related Substances at 230 nm ||||| Water Content | Appearance 24 hr After Reconstitution |
|---|---|---|---|---|---|---|---|---|---|---|---|---|
| | | | | | | Rep | RRT 0.19 | RRT 0.33 | RRT 0.41 | | | |
| 3 months at 2-8°C | Clear 20 mL glass vial with a grey stopper and blue flip off seal containing an off white cake, approximately 12mm in depth. Slight cracks on surface. | Clear colourless solution free from visible particles and fibres (one fibre observed) | Mean = 30 seconds | Rep 1 = 10.748 Rep 2 = 10.536 Mean pH = 10.64 | Rep 1 = 0.844mg/mL Rep 2 = 0.762mg/mL | 1 2 Total Area % = 0.14% Area | | 0.13 0.14 | nd nd | tr tr | Rep 1 = 1.8 mg/vial Rep 2 = 1.9 mg/vial Mean = 1.9 mg/vial | Clear colourless solution containing several small fibres but no visible particulates. Fibres not believed to be drug related |
| 3 months at 35°C/60%RH | Clear 20 mL glass vial with a grey stopper and blue flip off seal containing an off white cake, approximately 12.5mm in depth. Slight cracks on surface. | Clear colourless solution free from visible particles and fibres. | Mean = 30 seconds | Rep 1 = 10.664 Rep 2 = 10.700 Mean pH = 10.68 | Rep 1 = 0.795mg/mL Rep 2 = 0.832mg/mL Mean = 0.81 mg/mL | 1 2 Total Area % = 0.14% Area | | 0.15 0.15 | nd nd | tr tr | Rep 1 = 1.5 mg/vial Rep 2 = 1.4 mg/vial Mean = 1.5 mg/vial | Clear colourless solution containing several small fibres but no visible particulates. Fibres not believed to be drug related |

FIG. 7

| Timepoint/ Conditions | Appearance Before Reconstitution | Appearance After Reconstitution | Reconstitution Time | pH (after reconstitution) | Assay for Glibenclamide | Assay for Related Substances at 230 nm | | | | Water Content | Appearance 24 hr After Reconstitution |
|---|---|---|---|---|---|---|---|---|---|---|---|
| 3 months at 40°C/75%RH | Clear 20 mL glass vial with a grey stopper and blue flip off seal containing an off white cake, approximately 12mm in depth. Slight cracks on surface. | Clear colourless solution free from visible particles and fibres | Mean = 1mm 15 seconds | Rep 1 = 10.683 Rep 2 = 10.784 Mean pH = 10.73 | Rep 1 = 0.760mg/mL Rep 2 = 0.785mg/mL Mean = 0.77 mg/mL | Rep | RRT 0.19 | RRT 0.33 | RRT 0.41 | Rep 1 = 1.4 mg/vial Rep 2 = 1.5 mg/vial Mean = 1.5 mg/vial | Clear colourless solution containing several small fibres but no visible particulates. Fibres not believed to be drug related |
| | | | | | | 1 | 0.19 | nd | tr | | |
| | | | | | | 2 | 0.19 | nd | tr | | |
| | | | | | | Total Area % = 0.19% Area | | | | | |
| 3 months and 3 weeks and 3 days at 2-8°C | Not tested | Not tested | Not tested | Not tested | Rep 1 = 0.895mg/mL Rep 2 = 0.838mg/mL Rep 3 = Not tested Rep 4 = 0.785mg/mL | Not tested | | | | Not tested | Not tested |

FIG. 8

FORMULATIONS AND METHODS FOR LYOPHILIZATION AND LYOPHILATES PROVIDED THEREBY

CROSS REFERENCE TO RELATED APPLICATIONS

This application is a continuation of U.S. patent application Ser. No. 16/138,173, filed Sep. 21, 2018, now granted as U.S. Pat. No. 10,426,729, which is a continuation of U.S. patent application Ser. No. 14/508,488, filed Oct. 7, 2014, now granted as U.S. Pat. No. 10,117,834, which is a continuation of U.S. patent application Ser. No. 13/610,335, filed Sep. 11, 2012, now granted as U.S. Pat. No. 8,858,997, which is a continuation of U.S. patent application Ser. No. 12/746,164, filed Jun. 3, 2010, now granted as U.S. Pat. No. 8,277,845, which is a United States national phase application of International Patent Application No. PCT/US2008/085384, filed Dec. 3, 2008, which claimed priority to U.S. Provisional Patent Application No. 60/992,241, filed on Dec. 4, 2007, all of which are hereby incorporated herein by reference in their entireties.

BACKGROUND

Compounds that are weak acids are often poorly soluble at low (e.g., less than about pH 4 or pH 5) and at medium pH values (e.g., pH values of about 6 or 7). Such compounds are often difficult to use as pharmaceuticals due to, for example, poor solubility in pharmaceutically acceptable solutions. Thus, despite possible theoretical therapeutic efficacy, some compounds are not useful in clinical practice, or not as useful as they might be if methods and compositions were available to provide such compounds in pharmaceutically acceptable forms. In addition, formulations of such compounds may be unstable, and may be difficult to store for use, even if it were possible to prepare pharmaceutically acceptable formulations of such compounds.

Sulphonylureas and other compounds that act on sulphonylurea receptors (SURs) are useful in medical treatment of diabetes and other disorders. SURs may be of different types, including, for example, sulphonylurea receptor type 1 (SUR1) and sulphonylurea receptor type 2 (SUR2). Compounds that act at SURs include sulphonylureas (such as glibenclamide) and other compounds (e.g., repaglinide and taglizide). Sulphonylureas and other compounds active at SURs include glibenclamide (also known as glyburide), 4-trans-hydroxy-glibenclamide, 3-cis-hydroxy-glibenclamide, tolbutamide, repaglinide, nateglinide, meglitinide, midaglizole, LY397364, LY389382, glyclazide, glimepiride and other drugs or metabolites of drugs which interact with SURs.

In addition, ion channels such as potassium channels and non-selective channels may be associated with SURs (e.g., a $NC_{co\text{-}ATP}$ channel; see, for example, U.S. Pat. No. 7,285,574, hereby incorporated by reference in its entirety, or an ATP-sensitive potassium channel ($K_{ATP}$ channel)). Compounds active towards ion channels associated with SURs are also useful in medical treatments. Some compounds that act on non-selective channels that may be associated with SURs include, for example, pinkolant, flufenamic acid, mefanamic acid, niflumic acid, rimonabant, and SKF 9635. In addition, other compounds may act on or affect the action of SURs and/or ion channels associated with SURS, including, without limitation, for example, steroids and steroid derivatives and related compounds such as estrogen, estradiol, estrone, estriol, genistein, diethystilbestrol, coumestrol, zearalenone, non-steroidal estrogens, and phytoestrogens.

Glibenclamide Solubility

Glibenclamide solubility in various solutions has been reported, and is typically reported as being very poorly soluble in buffered aqueous solutions. For example, the solubility of glibenclamide in buffered aqueous solutions has been reported by Glomme et al. (Glomme A, Marz J, Dressman J B. Comparison of a miniaturized shake-flask solubility method with automated potentiometric acid/base titrations and calculated solubilities. J Pharm Sci. 2005 January; 94(1):1-16). The buffered aqueous solution was made with distilled water to form a potassium chloride (220 mM) solution buffered with potassium phosphate (29 mM), and the pH adjusted to pH 5, 6, or 7 with sodium hydroxide. These solutions had osmolarities of between about 280 to 310 milliOsmolar and had buffer capacities of about 10±2 milliEquvialents/L/pH. Glomme et al. report that glibenclamide is only sparingly soluble in such solutions, with extremely low solubilities at pH 2, 3, 5, 6, and 7, and relatively greater (although still very low) solubilities at pH 8, 9 and 11.8. These solubilities are shown in TABLE 1:

TABLE 1

Solubility of Glibenclamide at 37° C. (aqueous).

| pH | Solubility (mg/mL) |
|---|---|
| 2 | 0.00007 |
| 3 | 0.00006 |
| 5 | 0.0001 |
| 6 | 0.00062 |
| 7 | 0.00562 |
| 8 | 0.0512 |
| 9 | 0.0986 |
| 11.8 | 0.5316 |

It can be seen that glibenclamide in such aqueous solutions is poorly soluble, that the solubility is less at acidic pH, and that the solubility increases by an order of magnitude from pH 6 to pH 7, from pH 7 to pH 8, and from pH 8 to pH 11.8.

Similarly, low glibenclamide solubilities in aqueous solutions were reported by Kaiser et al. (Kaiser D G, Forist, A A. A review of Glibenclamide Metabolism in Man and Laboratory Animals. Physical and Analytical Chemistry Research, The Upjohn Company; 1975), with solubilities of below 1 mg/mL at all measured pH values from pH 4 to pH 9. Glibenclamide was dissolved in Britton-Robinson buffer. (Britton-Robinson buffer is an aqueous buffer solution including phosphoric acid, acetic acid and boric acid, with the pH adjusted with sodium hydroxide.) These solubilities are reported in TABLE 2.

TABLE 2

Solubility of Glibenclamide at 27° C. (aqueous).

| pH | Solubility (mg/mL) |
|---|---|
| 4 | 0.004 |
| 6 | 0.005 |
| 7 | 0.011 |
| 8 | 0.080 |
| 9 | 0.600 |

Rydberg et al. (Rydberg T, Jonsson A, Roder M, Melander A. Hypoglycemic activity of glibenclamide (Glibenclamide) metabolites in humans. Diabetes Care. 1994 September;

17(9):1026-30) also reported a glibenclamide solubility of 0.5 mg/mL in a 0.1 M, pH 10 phosphate-buffered aqueous solution (300 mOsm/L).

The following formulation for intravenous glibenclamide (1 mg/mL) was developed for a Mayo study (Schrage W G, Dietz N M, Joyner M J. Effects of combined inhibition of ATP-sensitive potassium channels, nitric oxide, and prostaglandins on hyperemia during moderate exercise. J Appl Physiol. 2006 May; 100(5):1506-12. Epub 2006 Feb. 9):

| Ingredient | Amount |
|---|---|
| Glibenclamide | 500 mg |
| Sodium Chloride 0.9% | 450 mL |
| 0.1N Sodium Hydroxide | 50 mL |
| Above formula makes | 500 mL |
| Type of container | 5 mL amber vial |
| Amount in each | 5 mL |
| Shelf life | Unknown |

The formulation can be prepared by: i) mixing sodium hydroxide and sodium chloride in water; ii) dissolving glibenclamide in the mixture, with slight warming to help dissolve it; iii) filter the solution through a 0.22 micron filter into sterile 5 mL amber vials; iv) stopper, cap and crimp. Sterility can be tested by using a Millipore system, and while working in the laminar flow hood: i) pass the test solution through the filter and flush with sterile saline injection three times; ii) crimp the hoses and inject the culture media into the container; iii) record the product information on form #11.31, and staple to the compounding formula; iv) perform a LAL test using a 1:20 dilution; v) quarantine for 14 days and check daily for presence or absence of growth; vi) record all culture results on the culture report form and the Microbial Culture Journal.

Betageri et al. (Betageri, G. V. et al. Enhancement of dissolution of glibenclamide by solid dispersion and lyophilization techniques, Int. J. Pharm. 126, 155-160 (1995)) evaluated increasing solubility of glibenclamide first by addition of various polyethylene glycol (PEG) and then via various PEG forms plus lyophilization. Betageri did not lyophilize glibenclamide on its own, and the procedures were performed at pH 7.4 in buffered solutions. Glibenclamide-PEG was found to be more soluble than glibenclamide alone. It is to be noted that all the Betageri formulations involve one or more PEG, and that the concentrations are very low.

Lyophilization

Lyophilization is a term used to describe methods and actions that provide dried materials, such as powders, from liquids containing solids or dissolved materials by freeze-drying (freezing a liquid containing dissolved or suspended material, and drying while frozen by sublimation) to provide a dry solid containing the dissolved or suspended material in solid form. Typically, aqueous solutions are used in lyophilization, although mixed aqueous/solvent solutions, and other liquid solutions, may be used. For example, a biological material may be lyophilized from a solution or suspension in which it is mixed with protective agents. Such a solution or suspension may then be frozen, and subsequently dehydrated by sublimation. Sublimation may optionally be followed by further drying steps.

Many materials and chemicals may be lyophilized. For example, dilute chemicals, including organic molecules such as drugs, hormones, proteins, nucleic acids (e.g., DNA and RNA), lipids, and carbohydrates or other molecules, may be lyophilized to provide a dried form of a chemical or mixture of chemicals. Biological samples may also be lyophilized. Typically, lyophilization methods include freeze-drying a liquid solution or suspension to provide a dry residue containing a high concentration of the dissolved or suspended compounds. In some cases, the solid provided by lyophilization may be or include a salt.

Lyophilization processes provide solids, such as powders, dried films, or cakes. Small particles may be obtained, if desired, from such powders, films, or cakes by procedures such as grinding or flaking.

However, some methods of lyophilization may be improved.

In addition, some materials may be difficult to lyophilize. Some materials, including some organic molecules useful in pharmaceutical applications and as medicaments, are difficult to dissolve or suspend in a solution, particularly in aqueous solutions of neutral or near-neutral pH, or in buffered aqueous solutions.

Thus, the need exists for improved methods of lyophilizing materials suitable for a wider range of materials than is presently available, and for particular desired materials and for desired types of materials.

SUMMARY OF THE INVENTION

Methods, compositions, and kits providing solutions and lyophilized formulations of compounds of interest are taught herein. Compounds of interest are often compounds that are poorly soluble at low and medium pH values, although more soluble at higher pH values. The methods, compositions, and kits provided herein provide pharmaceutically acceptable formulations, including solutions and lyophilized formulations, that solve the low solubility and low stability problems associated with pharmaceutical formulations of compounds that are poorly soluble at low and medium pH values.

Compounds of interest may be, for example, sulphonylurea compounds, ion channel-blocking compounds, steroid compounds, and other compounds having pharmaceutical activity. For example, methods, compositions and kits providing lyophilized formulations of sulphonylurea compounds are taught herein. In a further example, methods, compositions and kits providing lyophilized formulations of ion-channel blocking compounds are taught herein. In a still further example, methods, compositions and kits providing lyophilized formulations of sulphonylurea compounds together with steroid compounds are taught herein. In a yet further example, methods, compositions and kits providing lyophilized formulations of sulphonylurea compounds together with ion-channel blocking compounds and/or steroid compounds are taught herein. In another example, methods, compositions and kits providing lyophilized formulations of sulphonylurea compounds and/or ion channel blocking compounds, optionally along with a substantially pharmaceutically inert compound are taught herein.

Methods for lyophilizing compounds from liquid solutions, and products comprising lyophilized solids obtained from such lyophilized liquid solutions, are provided herein. In certain embodiments, hydrophobic organic molecules are dissolved in aqueous solutions and lyophilized to provide solid compositions containing high concentrations of the hydrophobic organic molecules. In certain embodiments, these solid compositions containing high concentrations of hydrophobic organic molecules are stable and are suitable for storage, e.g., suitable for storage for long periods of time. Such storage may be at ambient conditions, may be under controlled temperature, may be under controlled humidity, or other condition or set of conditions; and may be stored in a sealed container (e.g., a bottle or jar with a removable lid, a tubes, a capsule, a caplet, a vial, or other container), and may be in a sealed container under an inert gas (e.g., nitrogen, argon, helium, or other inert gas), or other container with or without other element or compound in the container.

Sulphonylureas and other compounds active at sulphonylurea receptors (SURs) include many chemicals that may be difficult to dissolve or suspend in an aqueous solution. Sulphonylureas and other compounds active at SURs include glibenclamide (also known as glyburide), tolbutamide, repaglinide, nateglinide, meglitinide, midaglizole, LY397364, LY389382, glyclazide, glimepiride and other drugs or metabolites of drugs which interact with SURs. Other compounds which may also exhibit similar problems with going into solution, and which may be suitable for use in the practice of embodiments of the invention, include compounds termed herein "ion channel-blocking" compounds, such as, for example, pinkolant, flufenamic acid, mefanamic acid, niflumic acid, rimonabant, and SKF 9635. In addition, steroids and steroid derivatives and related compounds may also be lyophilized following embodiments of methods of the invention; such steroids, steroid derivatives and related compounds include, without limitation, estrogen, estradiol, estrone, estriol, genistein, diethystilbestrol, coumestrol, zearalenone, non-steroidal estrogens, and phytoestrogens. In addition, mixed solutions, containing combinations of these compounds, or these compounds in combination with other compounds, may be lyophilized in embodiments of the methods and compositions having features of the invention.

In addition, solutions and lyophilized formulations having features of the invention may include compounds which act to maintain, or aid in maintaining, proper levels of blood glucose, or which act to raise, or aid in raising, blood levels of glucose, preferably to maintain or raise glucose levels in the blood of a subject at or near normal physiological levels. Such compounds include, for example, glucose itself, other carbohydrates, glucagon, and other compounds, and combinations thereof.

As disclosed herein, glucose thus may be included in solutions and lyophilized formulations having features of the invention as an element having pharmaceutical activity, and may also be included in solutions and lyophilized formulations having features of the invention for purposes other than as an element having pharmaceutical activity. Thus, glucose, which has physiological activity, and may act as a pharmaceutically active element of solutions and lyophilized formulations having features of the invention, may also be included in solutions and lyophilized formulations having features of the invention for purposes other than its physiological effects. For example, glucose may be included, and may be discussed herein as a "pharmaceutically inert" compound or a "substantially pharmaceutically inert" compound. Such reference to glucose recognizes, e.g., its osmotic, bulking, or other properties in addition to its pharmaceutical activities. It will be understood that glucose is an element that may be included both where active ingredients are discussed herein, and where substantially pharmaceutically inert ingredients are discussed herein.

In addition, solutions and lyophilized formulations having features of the invention may include compounds which are substantially pharmaceutically inert. As used herein, compounds that are "substantially pharmaceutically inert" include sugars such as glucose, fructose, mannose, galactose, mannitol, sorbitol, lactose, sucrose, trehalose, and other sugars, including mono-saccharides, di-saccharides, and other sugars; salts such as sodium chloride, potassium chloride, and other compounds which may be used in pharmaceutical solutions with little or no effect on the pharmacological activity of an active ingredient, but which may have effects on, for example, the osmolarity of the solution in which the substantially pharmaceutically inert compounds are included. Note that the designation of glucose as a "substantially pharmaceutically inert" compound is for convenience of reference only; glucose has physiological activity and may be included for pharmaceutical activity at the same time as, or in addition to, its utility as a "substantially pharmaceutically inert" compound.

Thus, for example, in embodiments, solutions and methods suitable for the practice of the invention may include solutions, lyophilized formulations, and kits including solutions and/or lyophilized formulations of glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, to lazamide, gliquidone, LY397364, LY389382, glyclazide, glimepiride, estrogen, estradiol, estrone, estriol, genistein, diethystilbestrol, coumestrol, zearalenone, non-steroidal estrogens, phyto estrogens, pinkolant, flufenamic acid, mefanamic acid, niflumic acid, rimonabant, SKF 9635, and combinations thereof. Furthermore, solutions and methods suitable for the practice of the invention may include solutions, lyophilized formulations, and kits including solutions and/or lyophilized formulations of glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, SKF 9635, and combinations thereof in which one or more substantially pharmaceutically inert compound is also present in the solution, lyophilized formulation, or kit.

Methods for lyophilizing compounds in liquid solutions may include steps of: a) preparing aqueous solutions of a compound of interest in the absence of buffer or in the presence of a weak buffer (e.g., less than about 2 mM); b) adjusting the pH to high values of pH in order to increase the solubility of the compound of interest; and c) freeze-drying the solution to provide a lyophilized solid composition. It will be understood that the term "compound of interest" as used herein may be any one of the compounds named in the previous paragraph, and may include mixtures and combinations of more than one compound, and may include mixtures and combinations including one or more of, for example, the compounds named in the preceding paragraph. For example, methods for lyophilizing compounds in liquid solutions include preparing aqueous solutions of glibenclamide in the absence of buffer, adjusting the pH to high values of pH in order to increase the solubility of the glibenclamide. In a further example, methods for lyophilizing compounds in liquid solutions may include steps of preparing aqueous solutions of glibenclamide and another compound such as, for example, pinkolant, in the absence of buffer, adjusting the pH to high values of pH in order to increase the solubility of these compounds. Adjusting the pH of the solution to high pH values may be achieved using sodium hydroxide, potassium hydroxide, lithium hydroxide, calcium hydroxide, magnesium hydroxide, or other agent suitable for increasing the pH of an aqueous solution. Once the compound of interest (or mixture of compounds) is dissolved, the pH of the solution may optionally be lowered, e.g., by addition of acid such as hydrochloric acid, sulfuric acid, acetic acid, or other acid. The resulting solution, prepared by any of the optional methods and having any of the optional compositions discussed herein, may be freeze-dried effective to provide a lyophilized solid. The reconstituted liquid may have a lower pH than that of the pre-lyophilized solution due to the lyophilization process, with the compound or compounds remaining in solution despite the lower pH.

Methods for lyophilizing compounds in liquid solutions may include steps of: a) adding a compound of interest to water in the absence of buffer; b) adjusting the pH to high values of pH in order to increase the solubility of the compound of interest; c) adding further amounts of a compound of interest; and d) freeze-drying the solution to provide a lyophilized solid composition. Methods for lyophilizing compounds in liquid solutions may also include steps of: a) adding a compound of interest to water in the absence of buffer; b) adjusting the pH to high values of pH in order to increase the solubility of the compound of interest; c) adding further amounts of a compound of interest; d) repeating steps a), b), and c) one or more times as needed to achieve a desired, or to achieve a maximal, concentration of the compound of interest in the aqueous solution; and d) freeze-drying the solution to provide a lyophilized solid composition.

Methods for lyophilizing compounds in liquid solutions may include steps of: a) adding a compound of interest to water in the absence of buffer or in the presence of a weak buffer (less than about 2 mM); b) adjusting the pH to high values of pH in order to increase the solubility of the compound of interest; c) allowing the liquid to sit for a period sufficient for the pH to reduce; (d) further adjusting the pH to high values of pH in order to increase the solubility of the compound of interest; and e) freeze-drying the solution to provide a lyophilized solid composition. Methods for lyophilizing compounds in liquid solutions may also include steps of: a) adding a compound of interest to water in the absence of buffer; b) adjusting the pH to high values of pH in order to increase the solubility of the compound of interest; c) allowing the liquid to sit for a period sufficient for the pH to reduce; (d) further adjusting the pH to high values of pH in order to increase the solubility of the compound of interest; e) repeating steps a), b), c) and d) one or more times as needed to achieve a desired, or to achieve a maximal, concentration of the compound of interest in the aqueous solution; and f) freeze-drying the solution to provide a lyophilized solid composition.

The pH can be measured at any of the aforementioned steps, a single time or multiple times. The pH can be adjusted at any of the aforementioned steps, a single time or multiple times. A compound of interest may be added to water, or to a water solution containing compound of interest, in the absence of buffer, a single time or multiple times. A compound of interest may be added to high-pH water, or a high-pH water solution, or to a high-pH water solution containing compound of interest, in the absence of buffer, a single time or multiple times.

Thus, in embodiments of the methods, compositions and kits of the invention, solutions and lyophilized formulations, and kits including such solutions and lyophilized formulations, may include, for example, sulphonylureas and other compounds active at SURs such as glibenclamide, tolbutamide, repaglinide, nateglinide, meglitinide, midaglizole, LY397364, LY389382, glyclazide, glimepiride and other drugs or metabolites of drugs which interact with SURs; may include ion channel blockers such as, for example, pinkolant, flufenamic acid, mefanamic acid, niflumic acid, rimonabant, and SKF 9635; may include estrogen, estradiol, estrone, estriol, genistein, diethystilbestrol, coumestrol, zearalenone, non-steroidal estrogens, phytoestrogens or other steroid compound; and may also include one or more substantially pharmaceutically inert compound such as, for example, glucose, fructose, mannose, galactose, mannitol, sorbitol, lactose, trehalose, sucrose, and other sugars, including mono-saccharides, di-saccharides, and other sugars, sodium chloride, potassium chloride, or other substantially pharmaceutically inert compound.

In further particular embodiments, methods for lyophilizing compounds in liquid solutions include a) preparing, in the absence of buffer, aqueous solutions of a compound of interest together with a substantially pharmaceutically inert compound, b) adjusting the pH to high values of pH in order to increase the solubility of the compound of interest, and c) freeze-drying the solution to provide a lyophilized solid composition. For example, methods for lyophilizing compounds in liquid solutions include preparing aqueous solutions of glibenclamide and mannitol in the absence of buffer, adjusting the pH to high values of pH in order to increase the solubility of the glibenclamide and mannitol compounds. In a further example, methods for lyophilizing compounds in liquid solutions include preparing aqueous solutions of glibenclamide and another compound in the absence of buffer, adjusting the pH to high values (e.g., pH of 8, 9, 10, or 11) in order to increase the solubility of the compound of interest. Adjusting the pH of the solution to a high pH value may be achieved using sodium hydroxide, potassium hydroxide, lithium hydroxide, calcium hydroxide, magnesium hydroxide, or other agent suitable for increasing the pH of an aqueous solution. Once the compound of interest (or mixture of compounds) is dissolved, the pH of the solution may optionally be lowered, e.g., by addition of acid such as hydrochloric acid, sulfuric acid, acetic acid, or other acid. The resulting solution, containing a compound of interest together with a substantially pharmaceutically inert compound, prepared by any of the optional methods and having any of the optional compositions discussed herein, may be freeze-dried effective to provide a lyophilized solid.

In further embodiments, methods for lyophilizing compounds in liquid solutions include a) preparing, in the presence of a buffer, aqueous solutions of a compound of interest (which may comprise a mixture of compounds of interest), b) adjusting the pH to high values of pH in order to increase the solubility of the compound of interest, and c) freeze-drying the solution to provide a lyophilized solid composition. Once the compound of interest is dissolved, the pH of the solution may optionally be lowered, e.g., by addition of acid. The resulting solution, containing a compound of interest together with a substantially pharmaceutically inert compound, prepared by any of the optional methods and having any of the optional compositions discussed herein, may be freeze-dried effective to provide a lyophilized solid.

In further embodiments, methods for lyophilizing compounds in liquid solutions include a) preparing, in the presence of a buffer, aqueous solutions of a compound of interest (which may comprise a mixture of compounds of interest) together with a substantially pharmaceutically inert compound, b) adjusting the pH to high values of pH in order to increase the solubility of the compound of interest, and c) freeze-drying the solution to provide a lyophilized solid composition. Once the compound of interest is dissolved, the pH of the solution may optionally be lowered, e.g., by addition of acid. The resulting solution, containing a compound of interest together with a substantially pharmaceutically inert compound, prepared by any of the optional methods and having any of the optional compositions discussed herein, may be freeze-dried effective to provide a lyophilized solid.

Kits having features of the invention may include liquid solutions of compounds of interest, and/or liquid solutions of mixtures of compounds of interest, and/or liquid solutions of compounds of interest together with one or more substantially pharmaceutically inert compound, and may include instructions for the use of such liquid solutions. For example, instructions for the use of such liquid solutions may include instructions for freeze-drying such solutions in order to obtain a lyophilized formulation of the compound or compounds of interest. Alternatively, or in addition, kits having features of the invention may include lyophilized formulations of compounds of interest, and/or lyophilized formulations of mixtures of compounds of interest, and/or lyophilized formulations of compounds of interest together with one or more substantially pharmaceutically inert compound, and may include instructions for the use of such lyophilized formulations. For example, instructions for the use of such lyophilized formulations may include instructions for re-constituting such lyophilized formulations to provide solutions, preferably sterile solutions, suitable for use in research and/or in pharmaceutical, medical, veterinary, or other clinical application. Kits may include in separate vials of a pH adjuster or of pH adjusters which are able to reduce the pH of the reconstituted solution, where a "pH adjuster" is a compound able to alter the pH of a water solution (e.g., sodium hydroxide, potassium hydroxide, hydrochloric acid, or other compounds effective to alter the pH of a water solution).

Solutions, formulations, lyophilates, and methods for making the same, as disclosed herein, are useful to provide, for example, materials that may be used as medicaments, and to prepare medicaments, for the treatment of diseases, disorders, and conditions. Sulphonylurea solutions, formulations, lyophilates, and methods for making the same, may be used as medicaments, and to prepare medicaments for treating, for example, stroke, brain trauma, spinal cord injury, ischemia (of the brain, of the spinal cord, of the heart, and of other organs), and any other disease or condition in which cells may express a SUR1-sensitive non-selective channel such as the $NC_{co-ATP}$ channel. Sulphonylurea solutions, formulations, lyophilates, and methods for making the same, may be used as medicaments, and to prepare medicaments for treating, for example, diabetes, for treating diseases or conditions affecting $K_{ATP}$ channels or which may be treated by modulating $K_{ATP}$ channels, and other conditions. Accordingly, the materials disclosed herein provide improved medicaments and treatments, and the methods disclosed herein provide improved methods for making medicaments and for treating patients.

Further embodiments relate to a lyophilized glibenclamide powder substantially free of buffer and including one or more substantially pharmaceutically inert compounds. In certain instances, the substantially pharmaceutically inert compounds are independently a sugar or a salt. In certain instances, the substantially pharmaceutically inert compounds are independently glucose, fructose, mannose, galactose, mannitol, sorbitol, lactose, trehalose, sucrose, sodium chloride, or potassium chloride. In certain instances, one of the substantially pharmaceutically inert compounds is mannitol. In certain instances, the powder includes only one substantially pharmaceutically inert compound, which is a sugar or a salt. In certain instances, the substantially pharmaceutically inert compound is mannitol. In certain instances, the amount of buffer is less than 1% w/w. In certain instances, the amount of buffer is less than 0.1% w/w. In certain instances, the amount of substantially pharmaceutically inert compounds is less than 10% w/w. In certain instances, the amount of substantially pharmaceutically inert compounds is less than 5% w/w. In certain instances, the amount of substantially pharmaceutically inert compounds is between 2% w/w and 6% w/w. In certain instances, the glibenclamide has a water solubility of at least about 0.01 mg/mL at 20° C. in an aqueous solution having a pH of 7. In certain instances, the substantially pharmaceutically inert compound is mannitol provided in the aqueous solution from which the glibenclamide powder was lyophilized in the amount of about 3 mg/100 mL (3%). In certain instances, the substantially pharmaceutically inert compound is glucose. In certain instances, the substantially pharmaceutically inert compound is glucose provided in the aqueous solution from which the glibenclamide powder was lyophilized in the amount of about 3 mg/100 mL (3%). In certain instances, the substantially pharmaceutically inert compound is a salt provided in the aqueous solution from which the glibenclamide powder was lyophilized in the amount of less than about 10 mg/100 mL (10%). In certain instances, the substantially pharmaceutically inert compound is sodium chloride or potassium chloride.

In certain instances, lyophilized glibenclamide powder is substantially free of agents enhancing the solubility of glibenclamide. Representative agents that may enhance the solubility of glibenclamide include cyclodextrins and solubilizing polymers, such as polyethylene glycol. In certain instances, lyophilized glibenclamide powder contains less than 1% w/w of agents enhancing the solubility of glibenclamide. In certain instances, lyophilized glibenclamide powder contains less than 0.1% w/w or less than 0.01% w/w of agents enhancing the solubility of glibenclamide.

Further embodiments relate to a solid pharmaceutical composition consisting essentially of a lyophilized glibenclamide powder, an alkali metal base, and optionally a substantially pharmaceutically inert bulking agent selected from the group consisting of a mono-saccharide and di-saccharide. In certain instances, the alkali metal base is sodium hydroxide or potassium hydroxide, and the substantially pharmaceutically inert bulking agent is mannitol, glucose, fructose, mannose, galactose, sorbitol, lactose, trehalose, or sucrose. In certain instances, the substantially pharmaceutically inert bulking agent is mannitol. In certain instances, the amount of substantially pharmaceutically inert bulking agent is between 2% w/w and 6% w/w. In certain instances, the amount of alkali metal base is less than 10% w/w. In certain instances, the amount of alkali metal base is less than 5% w/w.

Further embodiments relate to a pharmaceutical composition comprising a lyophilized glibenclamide powder and another pharmaceutically active compound, the composition being substantially free of buffer. In certain instances, the other pharmaceutically active compound is 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phyto estrogens, pinkolant, flufenamic acid, mefanamic acid, niflumic acid, rimonabant, or SKF 9635. In certain instances, the other pharmaceutically active compound is 4-trans-hydroxy-glibenclamide, 3-cis-hydroxy-glibenclamide, tolbutamide, repaglinide, nateglinide, meglitinide, midaglizole, LY397364, LY389382, glyclazide, or glimepiride.

Further embodiments relate to a method for lyophilizing a compound, comprising: a) preparing an aqueous solution of a compound in the absence of buffer, b) adjusting the pH to greater than about 8 in order to increase the solubility of the compound, and c) freeze-drying the solution to provide a lyophilized solid composition. In certain instances, the pH is greater than about 9. In certain instances, the pH is greater than about pH 10. In certain instances, the concentration of the compound in solution is greater than about 0.5 mg/mL. In certain instances, the concentration of the compound in solution is greater than about 1 mg/mL. In certain instances, the concentration of the compound in solution is greater than about 2 mg/mL. In certain instances, the concentration of the compound in solution is greater than about 4 mg/mL. In certain instances, the compound is glibenclamide, 4-trans-hydroxy-glibenclamide, 3-cis-hydroxy-glibenclamide, tolbutamide, chlorpropamide, to lazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, or SKF 9635. In certain instances, the compound is glibenclamide.

Further embodiments relate to an aqueous pharmaceutical composition comprising lyophilized glibenclamide powder, water, an alkali metal salt, and a substantially pharmaceutically inert bulking agent selected from the group consisting of a mono-saccharide and di-saccharide, the composition containing less than 1% w/v of a buffering agent. In certain instances, the alkali metal salt is sodium chloride or potassium chloride, and the substantially pharmaceutically inert bulking agent is mannitol, glucose, fructose, mannose, galactose, sorbitol, lactose, trehalose, or sucrose. In certain instances, the substantially pharmaceutically inert bulking agent is mannitol. In certain instances, the amount of substantially pharmaceutically inert bulking agent is between 2% w/v and 15% w/v. In certain instances, the amount of substantially pharmaceutically inert bulking agent is between 2% w/v and 6% w/v. In certain instances, the amount of alkali metal salt is less than 5% w/v. In certain instances, the pH of the composition is about 6 to about 8. In certain instances, the pH of the composition is 6.5 to 8.0. In certain instances, the osmolality of the composition is 200 mOsm to 400 mOsm. In certain instances, the osmolality of the composition is 250 mOsm to 330 mOsm. In certain instances, the composition further comprises glucose in the amount of 2% w/v to 10% w/v. In certain instances, the substantially pharmaceutically inert bulking agent is glucose.

In certain embodiments, the compositions described herein include glucose or a related carbohydrate, glucagon, or a combination thereof. Glucose or a related carbohydrate, glucagon, or a combination thereof may serve as excipients. In certain embodiments, the glucose or related carbohydrate, glucagon, or combination thereof may be present in an amount sufficient to provide a therapeutic effect and/or therapeutic benefit along with the sulphonylurea compound. For example, co-administration of a sulphonylurea with a therapeutically effective amount of glucose or a related carbohydrate, glucagon, or combination thereof may be helpful and/or effective to maintain appropriate levels of serum glucose in the blood of a patient to which the formulation is administered. Appropriate levels of blood glucose are, for example, within the range of about 60 mg/dl (milligrams per deciliter) to about 150 mg/dl (about 3.3 mM (millimoles per liter) to about 8 mM glucose). Thus, glucose or a related carbohydrate, glucagon, or combinations thereof when further combined with a sulphonylurea compound may be administered in combination to maintain the serum glucose within this range while providing the therapeutic benefits of the sulphonylurea compounds.

For example, as disclosed in U.S. Pat. No. 7,285,574, administration of sulphonylurea compounds to a subject in need thereof may be helpful and/or effective to reduce the risk of stroke and/or hypoxia/ischemia, reduce the amount of damage following stroke and/or hypoxia/ischemia (e.g., reduce intracranial pressure, reduce cell death, reduce stroke size, and/or reduce spinal cord injury, etc). A suitable amount of glucose, related carbohydrate, glucagon, or combination thereof, comprises an amount that maintains a reasonable level of blood glucose in the patient, for example, the amount of glucose, related carbohydrate, glucagon, or a combination thereof maintains a blood glucose level of at least about 60 mg/dl, more preferably, is effective to maintain blood glucose levels within an acceptable range, such as, for example, between about 60 mg/dl and about 150 mg/dl. Thus, the amount of glucose, related carbohydrate, glucagon, or a combination thereof is helpful and/or effective to prevent the subject from becoming hypoglycemic.

In certain embodiments, formulations having features of the invention may include a sulphonylurea compound or compounds, in combination with an additional therapeutic agent, such as tissue plasminogen activator (tPA) or functionally related compound, aspirin, statins, diuretics, warfarin, Coumadin, mannitol, etc. Further embodiments may include formulations including a) a sulphonylurea compound or compounds, b) a thrombolytic agent, and c) glucose, a related carbohydrate, glucagon, or a combination thereof.

Further embodiments relate to a method of treating a patient suffering from a disorder selected from the group consisting of stroke, neuronal cell swelling, traumatic brain injury, spinal cord injury, organ ischemia, acute coronary syndrome, myocardial infarction, sepsis, and diabetes, comprising administering intravenously to a patient in need thereof an effective amount of an aqueous pharmaceutical composition described herein. In certain instances, the disorder is stroke. In certain instances, the patient is a human. In certain other instances, the disorder is stroke, ischemia, hypoxia/ischemia, spinal cord injury, brain trauma, or other brain injury. In certain embodiments, the composition administered to the patient comprises a sulphonylurea compound and optionally glucose, carbohydrate related to glucose, glucagon, or a combination thereof. In further embodiments, such formulations may comprise a) a sulphonylurea compound or compounds, b) glucose, a carbohydrate related to glucose, glucagon, or a combination thereof, and c) another therapeutic agent. In certain instances, the glucose, carbohydrate related to glucose, glucagon, or a combination thereof is present in a therapeutically effective amount.

Further embodiments relate to a vial of glibenclamide powder packaged with a vial of diluent. Further embodiments relate to a vial of glibenclamide powder packaged with a vial of diluent, where the diluent is selected from the group consisting of water; water and alcohol; water and glucose; and water, PEG and alcohol. In certain instances, the diluent is water and glucose. In certain instances, the glucose is present in the amount of between about 2% and about 15% as measured by weight per volume (w/v). In certain instances, the diluent is a 5% dextrose solution. Other embodiments relate to a vial of glibenclamide powder packaged with a vial of diluent, where the pH of the diluent has a pH of about 7.4 or greater. Still other embodiments relate to a vial of glibenclamide powder packaged with a vial of diluent, where the diluent has a pH of about pH 7.4 or greater and is buffered. In certain instances, the buffer concentration is between about 1 mM and about 100 mM. In certain instances, the buffer concentration is less than about 15 mM. In certain instances, the buffer concentration is between about 5 mM and about 10 mM.

Further embodiments relate to a vial of glibenclamide powder packaged with a vial of diluent, where the diluent has a pH of about 7.4 or greater and is buffered with a pharmaceutically acceptable buffer. Further embodiments relate to a vial of glibenclamide powder packaged with a vial of diluent, where the diluent has a pH of about 7.4 or greater and is buffered with a buffer selected from meglumine and diethanolamine. Further embodiments relate to a vial of glibenclamide powder packaged with a vial of diluent, where the diluent has a pH of about 7.4 and is buffered with a buffer selected from meglumine and diethanolamine. Further embodiments relate to a vial of micronized glibenclamide powder packaged with a vial of diluent, where the diluent has a pH of about 7.4 or greater and is buffered with a buffer selected from meglumine and diethanolamine. Further embodiments relate to a vial of micronized glibenclamide powder packaged with a vial of diluent, where the diluent has a pH of about 7.4 and is buffered with a buffer selected from meglumine and diethanolamine. Further embodiments relate to a vial containing lyophilized glibenclamide, a bulking agent, and a pH adjuster. Further embodiments relate to a vial containing lyophilized glibenclamide, a bulking agent, and a pH adjuster, wherein the pH is adjusted using NaOH. Further embodiments relate to a vial containing lyophilized glibenclamide, a bulking agent, and a pH adjuster, wherein the concentration of glibenclamide is about 1 mg/mL. In certain instances, the bulking agent is mannitol. In certain instances, the pH prior to lyophilization is about pH 11.4. In certain instances, the starting material is micronized glibenclamide. In certain instances, the vial is packaged with a vial of diluent (buffered or not) with a pH of 7.4-8.0 to add to the product above following reconstitution to reduce pH.

Further embodiments relate to a kit comprising: a lyophilized formulation of a compound as described herein; a diluent solution; and instructions for the use of such liquid solutions. In certain instances, said diluent solution is selected from water; water and alcohol; water and polyethylene glycol (PEG); water and glucose; and water, alcohol and PEG. In certain instances, the diluent solution is water and glucose. In certain instances, the glucose is present in the amount of between about 2% and about 15% as measured by weight per volume (w/v). In certain instances, the diluent is a 5% dextrose solution. In certain instances, the diluent comprising alcohol, where alcohol is ethanol. In certain instances the pH of the diluent is about 7.4 or greater. In certain instances, the diluent is buffered. In certain instances, the buffer concentration is between about 1 mM and about 100 mM. In certain instances, the buffer concentration is less than about 15 mM. In certain instances, the buffer concentration is between about 5 mM and about 10 mM. In certain instances, the diluent has a pH of about 7.4 or greater and is buffered with a pharmaceutically acceptable buffer.

Further embodiments relate to a liquid formulation consisting essentially of glibenclamide and water, the formulation having a pH that is sufficiently high so that a change in pH of about 1 does not cause glibenclamide to precipitate from the solution. In certain instances, the formulation contains less than about 0.01% w/v of a buffer. In certain instances, the formulation contains less than about 0.01% w/v of a surfactant. In certain instances, the formulation contains less than about 0.01% w/v of a cosolvent. In certain instances, the pH of the formulation is greater than about 9. In certain instances, the pH of the formulation is greater than about 10. Further embodiments relate to a lyophilate composition produced by lyophilizing one of the formulations described above. Still further embodiments relate to a liquid pharmaceutical composition produced by reconstituting a lyophilate composition described herein, wherein the pH of said liquid pharmaceutical composition is sufficiently high to dissolve at least about 98% by weight of the lyophilate composition. In certain instances, the liquid pharmaceutical composition has a pH in the range of about 6 to about 8, comprises saline, and at least 98% w/v of glibenclamide is dissolved.

Further embodiments relate to a liquid formulation consisting essentially of glibenclamide and water, the formulation having a pH that is sufficiently high so that a change in pH of about 1 does not cause glibenclamide to precipitate from the solution, the formulation further characterized in that the solution is suitable for lyophilization to form a lyophilate that can be reconstituted and diluted with saline to form a solution having a pH in the range about 6 to about 8 and the glibenclamide remains dissolved in solution. Other embodiments relate to a lyophilized glibenclamide powder produced by lyophilizing a liquid solution consisting essentially of glibenclamide and one or more substantially pharmaceutically inert compounds, the liquid solution having a pH greater than 9. In certain instances, the liquid solution contains less than about 0.01% w/v of a buffer. In certain instances, the liquid solution has a pH greater than 10.

Further embodiments relate to a liquid formulation consisting essentially of an active therapeutic agent and one or more substantially pharmaceutically inert compounds, the liquid formulation having a pH greater than 8, and wherein the active therapeutic agent is a weak acid. In certain instances, the liquid formulation contains less than about 0.01% w/v of a buffer. In certain instances, the liquid formulation has a pH greater than 9. In certain instances, the active compound is an organic compound having a molecular weight of less than 500 g/mol and comprising a sulphonylurea group. In certain instances, the active compound is glibenclamide. Other embodiments relate to a lyophilized glibenclamide powder produced by lyophilizing the liquid formulation described above.

Formulations, compositions, and contents of kits as disclosed herein are suitable as formulations and compositions, and/or for use in preparing pharmaceutical formulations and compositions, for administration to a patient in need of treatment. For example, a patient in need of treatment may be a patient in need of treatment with an effective amount of an aqueous pharmaceutical composition described herein. A patient in need of treatment may be, for example, any patient for whom a sulphonylurea compound may provide therapeutic benefit, including, for example, a patient suffering from diabetes, ischemia, hemorrhage, or other disorder or condition susceptible of treatment with a sulphonylurea compound. A patient in need of treatment may be, for example, any patient for whom a combination of a sulphonylurea compound together with an ion-channel blocking compound may provide therapeutic benefit. A patient in need of treatment may be, for example, any patient for whom a combination of a sulphonylurea compound together with an ion-channel blocking compound and/or steroid compound may provide therapeutic benefit. In another example, a patient in need of treatment may be, for example, any patient for whom a combination of a sulphonylurea compound and/or an ion channel blocking compound, along with a substantially pharmaceutically inert compound may provide therapeutic benefit.

A patient in need of treatment may be, for example, a patient suffering from diabetes, or from hemorrhage, or other disorder or condition. A patient in need of treatment may be, for example, a patient suffering from ischemia of any organ, or organs, or system. Such a system may be, for example, the nervous system, including a portion of the nervous system, or the cardiovascular system, or a part of the cardiovascular system. Such an organ may be, for example, the brain, the heart, a muscle, or other organ. A patient in need of treatment may be any patient who may benefit from administration of the formulations, compositions, and/or contents of the kits disclosed herein. Further examples of a patient in need of treatment include patients suffering from a disorder selected from the group consisting of stroke, hemorrhage, neuronal cell swelling, traumatic brain injury, spinal cord injury, organ ischemia, acute coronary syndrome, myocardial infarction, sepsis, and diabetes.

Another aspect of the invention relates to methods of processing a claim under a health insurance policy. In general, the processing of an insurance claim for the coverage of a medical treatment or drug therapy involves notification of the insurance company, or any other entity, that has issued the insurance policy against which the claim is being filed, that the medical treatment or drug therapy will be performed. A determination is then made as to whether the medical treatment or drug therapy that will be performed is covered under the terms of the policy. If covered, the claim is then processed, which can include payment, reimbursement, or application against a deductable. Accordingly, certain embodiments relate to a method for processing a claim under a health insurance policy submitted by a claimant seeking reimbursement for costs associated with treatment using a composition or kit described herein, the method comprising: a) reviewing said claim; b) determining whether said treatment is reimbursable under said insurance policy; and c) processing said claim to provide partial or complete reimbursement of said costs.

For example, embodiments of the invention include methods for processing claims for medical insurance and/or reimbursement for purchase or prescription of any of the formulations, compositions and kits disclosed herein. In specific embodiments, the methods employ a computer for said processing of an insurance claim and/or for reimbursement for purchase or for prescription of any of the formulations, compositions and kits disclosed herein. Further embodiments relate to methods for processing claims for medical insurance and/or reimbursement for purchase or prescription of any of the formulations, compositions and kits disclosed herein for treating a patient in need of treatment.

As disclosed herein, a method for processing claims for medical insurance and/or reimbursement for purchase or prescription of any of the formulations, compositions and kits disclosed herein may include the steps of:
i) receiving a claim for medical insurance and/or reimbursement for purchase or prescription of a formulation, composition, or kit as disclosed herein; and
ii) providing reimbursement for the medical treatment, procedure, and/or medicament.

In a further embodiment, a method for processing claims for medical insurance and/or reimbursement for purchase or prescription of any of the formulations, compositions and kits disclosed herein may include the steps of:
i) receiving a claim for medical insurance and/or reimbursement for purchase or prescription of a formulation, composition, or kit as disclosed herein;
ii) evaluating the claim; and
iii) providing reimbursement for the medical treatment, procedure, and/or medicament.

In embodiments of these methods for processing an insurance claim, any one or more of the steps may involve the use of a computer; any one or more of the steps may involve the use of electronic data transfer; any one or more of the steps may involve the use of a telephone and/or facsimile device; any one or more of the steps may involve the use of mail and/or of a delivery service; and any one or more of the steps may involve the use of electronic fund transfer devices and/or methods.

BRIEF DESCRIPTION OF THE FIGURES

FIG. 4 is a table listing characterization data obtained from a study evaluating the stability of lyophilized glibenclamide as described in example 7.

FIG. 5 is a table listing characterization data obtained from a study evaluating the stability of lyophilized glibenclamide as described in example 7.

FIG. 6 is a table listing characterization data obtained from a study evaluating the stability of lyophilized glibenclamide as described in example 7.

FIG. 7 is a table listing characterization data obtained from a study evaluating the stability of lyophilized glibenclamide as described in example 7.

FIG. 8 is a table listing characterization data obtained from a study evaluating the stability of lyophilized glibenclamide as described in example 7.

DETAILED DESCRIPTION

Figure 1:
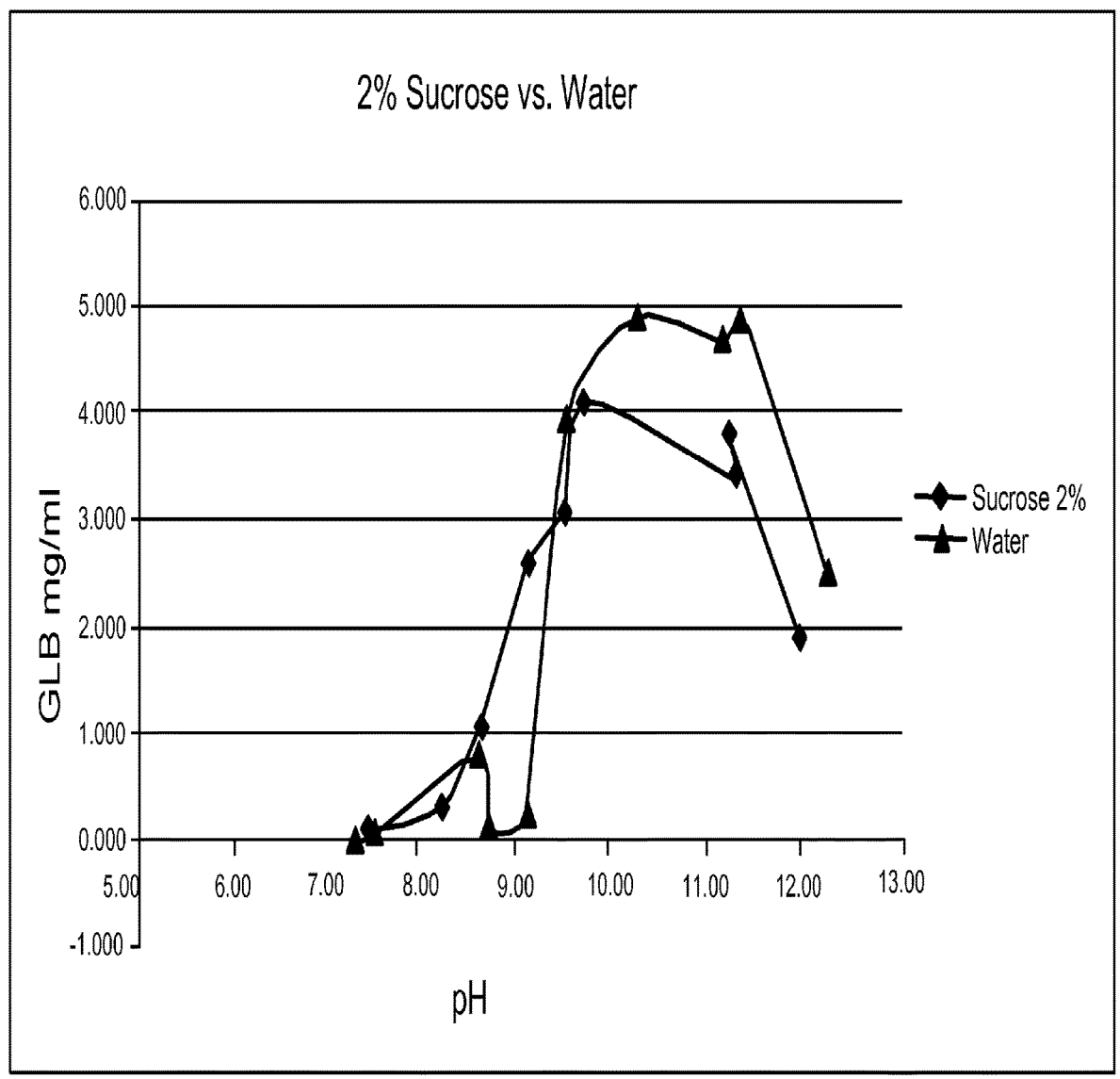
FIG. 1 shows glibenclamide concentration (shown in units of mg/mL on the vertical axis) plotted as a function of pH in an aqueous sucrose solution (2% sucrose in water, where "%" means g/100 mL) and in water alone.

Methods for lyophilization, solutions suitable as starting materials for lyophilization, dry materials and formulations resulting from lyophilization, including powders, cakes, films, and salts, and other methods, materials, and formulations are provided herein.

An exemplary compound which may be formulated into a solution suitable for lyophilization according to embodiments of the methods disclosed herein is glibenclamide. Glibenclamide (5-chloro-N-[2-[4-(cyclohexylcarbamoylsulfamoyl) phenyl]ethyl]-2-methoxy-benzamide; also known as glyburide) is a sulphonylurea compound having a molecular weight of 494 g/mol, a pKa of 6.8, a melting point of about 169-174° C., and has the following chemical structure:

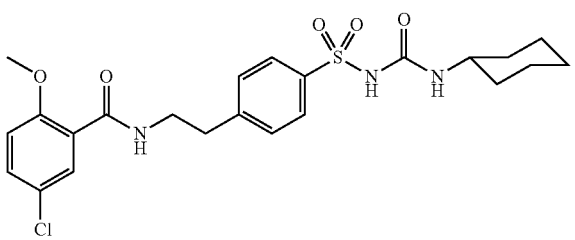 [SMILES: COc1ccc(Cl)cc1C(=O)NCCc1ccc(S(=O)(=O)NC(=O)NC2CCCCC2)cc1]

Glibenclamide has a water solubility of 4 mg/L and an ethanol solubility of 5 mg/mL. As such, glibenclamide is about three orders of magnitude more soluble in ethanol than in water. The terms "glibenclamide" and "glyburide" are intended to encompass both the free base compound and pharmaceutically acceptable basic salts thereof. In certain embodiments, the glibenclamide is present substantially in the form of the free base compound.

It is desirable to provide aqueous solutions of glibenclamide and of other drugs and compounds that are only sparingly soluble in aqueous solutions. For example, it is desirable to provide aqueous solutions of glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, SKF 9635, and combinations thereof.

For example, glibenclamide solutions, formulations, and lyophilates may be prepared, including solutions and formulation which may be water solutions of glibenclamide, without sugars, salts, or buffers; may be water solutions of glibenclamide also including a sugar (e.g., one or more of glucose, fructose, mannose, galactose, mannitol, sorbitol, lactose, trehalose, sucrose, and other sugars, including mono-saccharides, di-saccharides, and other sugars), may be water solutions of glibenclamide also including a salt (e.g., sodium chloride or potassium chloride), may be water solutions of glibenclamide also including a buffer (e.g., a Britton-Robinson buffer, a phosphate buffer, a "Tris" buffer (containing Tris(hydroxymethyl)aminomethane), a HEPES buffer (containing N-(2-Hydroxyethyl)piperazine-N'-(2-ethanesulfonic acid), or other buffer). It will be understood that such solutions, formulations, and lyophilates made from such solutions and formulations, may include combinations of the above.

As discussed above, Rydberg et al. report formulations of glibeneclamide in phosphate-buffered solutions. However, attempts by the present inventor to prepare formulations similar to those of Rydberg et al. revealed that phosphate-buffered glibenclamide lyophilizates did not reconstitute sufficiently. In addition, attempts by the present inventor to replicate the formulation of Schrage et al. (as reported in the Mayo study) were unsuccessful, possibly because the glibenclamide would not dissolve sufficiently.

In contrast to previous pH-adjusted, lyophilized products that use pH stabilizers or buffers to keep the pH constant, one aspect of the invention features a glibenclamide formulation lacking a buffering agent because it has been surprisingly discovered that such formulations are better suited for lyophilization and subsequent reconstitution to make a formulation suitable for intravenous administration. It has been found that a reduction in pH during lyophilization of glibenclamide formulations described herein does not adversely affect the ability to reconstitute the end product. Moreover, the invention overcomes a disadvantage of certain previously described buffered solutions—the disadvantage being that such buffered solution are often not suitable for dilution following reconstitution to form solutions with suitable pH values for extended-length intravenous infusion (e.g., 1 day, 3 days, 5 days). It is noted that very lightly buffered solutions (e.g., less than about 2 mM of buffering agent) are contemplated to be amenable to the present invention.

Accordingly, new methods and compositions providing aqueous solutions of glibenclamide and of other drugs and compounds that are otherwise only sparingly soluble in aqueous solutions are described herein. Exemplary methods, solutions, formulations, lyophilates, and compositions are described with particularity in the following examples.

The invention having been described generally will be described in reference to the various embodiments described below. The embodiments described below are presented for the purpose of further describing various aspects of the invention and should not be construed as limiting the scope of the invention.

One aspect of the invention relates to a formulation suitable for lyophilization which contains glibenclamide, one or more pH adjusters and a bulking agent. In certain instances, the pH adjuster is NaOH and the bulking agent is mannitol, sucrose, lactose or trehalose. In certain instances, the concentration of glibenclamide is 1 mg/mL, and the pH is 11.4. In certain instances, the pH adjusters are NaOH and HCl and the bulking agent is mannitol, sucrose, lactose or trehalose. In certain instances, the concentration of glibenclamide is 0.2 mg/mL and the pH is 9.4.

Another aspect of the invention relates to a vial containing the lyophilized contents of the above formulation. In certain instances, said vial is packaged with a vial of diluent. In certain instances, the diluent has a pH of about pH 7.4 or greater and is buffered.

Another aspect of the invention relates to a method of preparing a solution suitable for lyophilization of a drug active at a sulphonylurea receptor (SUR), comprising the steps of a) preparing a water solution having a pH of about pH 8 or greater; b) adding a drug to the water solution; and c) adjusting the pH of the resulting solution to have a pH of about 8 or greater; whereby a solution suitable for lyophilization of a drug active at a sulphonylurea receptor (SUR) is obtained. In certain instances, the pH is about 9 or greater.

Another aspect of the invention relates to a vial of Glibenclamide powder packaged with a vial of diluent. Certain other aspects of the invention relate to a vial of Glibenclamide powder packaged with a vial of diluent, where the diluent is selected from the group consisting of water; water and alcohol; and water, PEG and alcohol. Certain other aspects of the invention relate to a vial of Glibenclamide powder packaged with a vial of diluent, where the pH of the diluent has a pH of about pH 7.4 or greater. Still other aspects of the invention relate to a vial of Glibenclamide powder packaged with a vial of diluent, where the diluent has a pH of about pH 7.4 or greater and is buffered. In certain instances, the buffer concentration is between about 1 mM and about 100 mM. In certain instances, the buffer concentration is less than about 15 mM. In certain instances, the buffer concentration is between about 5 mM and about 10 mM.

Another aspect of the invention relates to a vial of glibenclamide powder packaged with a vial of diluent, where the diluent has a pH of about pH 7.4 or greater and is buffered with a pharmaceutically acceptable buffer. Certain other aspects of the invention relate to a vial of Glibenclamide powder packaged with a vial of diluent, where the diluent has a pH of about pH 7.4 or greater and is buffered with a buffer selected from meglumine and diethanolamine. Still other aspects of the invention relate to a vial of Glibenclamide powder packaged with a vial of diluent, where the diluent has a pH of about pH 7.4 or greater and is buffered with a buffer selected from meglumine and diethanolamine.

Another aspect of the invention relates to a glibenclamide powder substantially free of buffer. Certain other aspects of the invention relate to a glibenclamide powder substantially free of buffer and including a substantially pharmaceutically inert compound. In certain instances, the substantially pharmaceutically inert compound is selected from a sugar and a salt. In certain instances, the substantially pharmaceutically inert compound is selected from glucose, fructose, mannose, galactose, mannitol, sorbitol, lactose, trehalose, sucrose, and other sugars, including mono-saccharides, di-saccharides, and other sugars, sodium chloride, and potassium chloride. In certain instances, the substantially pharmaceutically inert compound is mannitol. In certain instances, the substantially pharmaceutically inert compound is mannitol provided in the aqueous solution from which the glibenclamide powder was lyophilized in the amount of about 3 mg/100 mL (3%). In certain instances, the substantially pharmaceutically inert compound is glucose. In certain instances, the substantially pharmaceutically inert compound is glucose provided in the aqueous solution from which the glibenclamide powder was lyophilized in the amount of about 3 mg/100 mL (3%). In certain instances, the substantially pharmaceutically inert compound is a sugar provided in the aqueous solution from which the glibenclamide powder was lyophilized in the amount of less than about 10 mg/100 mL (10%). In certain instances, the substantially pharmaceutically inert compound is a sugar provided in the aqueous solution from which the glibenclamide powder was lyophilized in the amount of less than about 5 mg/100 mL (5%). In certain instances, the substantially pharmaceutically inert compound is a salt. In certain instances, the substantially pharmaceutically inert compound is a salt selected from sodium chloride and potassium chloride. In certain instances, the substantially pharmaceutically inert compound is a salt provided in the aqueous solution from which the glibenclamide powder was lyophilized in the amount of less than about 10 mg/100 mL (10%). In certain instances, the substantially pharmaceutically inert compound is a salt provided in the aqueous solution from which the glibenclamide powder was lyophilized in the amount of less than about 5 mg/100 mL (5%). In certain instances, the substantially pharmaceutically inert compound is a salt provided in the aqueous solution from which the glibenclamide powder was lyophilized in the amount of less than or equal to about 2 mg/100 mL (2 N.

Another aspect of the invention relates to a glibenclamide powder (micronized or non micronized) substantially free of buffer and including another pharmaceutically active compound. In certain instances, the other pharmaceutically active compound is selected from 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, and SKF 9635. In certain instances, the other pharmaceutically active compound is selected from 4-trans-hydroxy-glibenclamide, 3-cis-hydroxy-glibenclamide, tolbutamide, repaglinide, nateglinide, meglitinide, midaglizole, LY397364, LY389382, glyclazide, and glimepiride. In certain instances, the other pharmaceutically active compound is selected from pinkolant, flufenamic acid, mefanamic acid, niflumic acid, rimonabant, and SKF 9635. In certain instances, the other pharmaceutically active compound is selected from estrogen, estradiol, estrone, estriol, genistein, diethystilbestrol, coumestrol, zearalenone, non-steroidal estrogens, and phytoestrogens.

Another aspect of the invention relates to a method for lyophilizing a compound, comprising: a) preparing an aqueous solution of a compound of interest in the absence of buffer, b) adjusting the pH to high values of pH in order to increase the solubility of the compound, and c) freeze-drying the solution to provide a lyophilized solid composition.

In certain instances, a high value of pH comprises a pH value greater than about pH 7.4. In certain instances, a high value of pH comprises a pH value greater than about pH 8. In certain instances, a high value of pH comprises a pH value greater than about pH 8.5. In certain instances, a high value of pH comprises a pH value greater than about pH 9. In certain instances, a high value of pH comprises a pH value greater than about pH 9.5. In certain instances, a high value of pH comprises a pH value greater than about pH 10. In certain instances, the concentration of the compound in solutions having high values of pH is greater than about 0.3 mg/mL. In certain instances, the concentration of the compound in solutions having high values of pH is greater than about 0.5 mg/mL. In certain instances, the concentration of the compound in solutions having high values of pH is greater than about 1 mg/mL. In certain instances, the concentration of the compound in solutions having high values of pH is greater than about 2 mg/mL. In certain instances, the concentration of the compound in solutions having high values of pH is greater than about 3 mg/mL. In certain instances, the concentration of the compound in solutions having high values of pH is greater than about 4 mg/mL. In certain instances, the concentration of the compound in solutions having high values of pH is greater than about 5 mg/mL. In certain instances, the compound of interest is selected from glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, and SKF 9635. In certain instances, the compound of interest comprises more than one pharmaceutically active compound.

Another aspect of the invention relates to a method for lyophilizing a compound, comprising: a) adding a compound of interest to water in the absence of buffer to provide an aqueous solution of the compound of interest; b) adjusting the pH to high values of pH; c) adding an additional amount of the compound of interest to said aqueous solution water of the compound of interest; and d) freeze-drying the solution to provide a lyophilized solid composition. Certain other aspects of the invention relate to a method for lyophilizing a compound, comprising: a) adding a compound of interest to water in the absence of buffer to provide an aqueous solution of the compound of interest; b) adjusting the pH to high values of pH; c) adding an additional amount of the compound of interest to said aqueous solution water of the compound of interest; d) repeating steps a), b), and c) one or more times as needed to achieve a desired, or to achieve a maximal, concentration of the compound of interest in the aqueous solution; and e) freeze-drying the solution to provide a lyophilized solid composition.

In certain instances, the compound of interest is selected from glibenclamide, 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, and SKF 9635. In certain instances, the compound of interest comprises more than one pharmaceutically active compound. In certain instances, the aqueous solution comprises a substantially pharmaceutically inert compound. In certain instances, the substantially pharmaceutically inert compound is selected from a sugar and a salt. In certain instances, the substantially pharmaceutically inert compound is selected from glucose, fructose, mannose, galactose, mannitol, sorbitol, lactose, trehalose, sucrose, and other sugars, including mono-saccharides, di-saccharides, and other sugars, sodium chloride, and potassium chloride. In certain instances, the substantially pharmaceutically inert compound in the aqueous solution has a concentration of about 10 mg/100 mL (10%). In certain instances, the substantially pharmaceutically inert compound in the aqueous solution has a concentration of about 5 mg/100 mL (5%). In certain instances, the substantially pharmaceutically inert compound in the aqueous solution has a concentration of about 3 mg/100 mL (3%). In certain instances, the substantially pharmaceutically inert compound in the aqueous solution has a concentration of about 1 mg/100 mL (1%).

Another aspect of the invention relates to a kit comprising: a liquid formulation of a compound of interest as described herein; and instructions for the use of such liquid solutions. Certain other aspects of the invention relate to a kit comprising: a lyophilized formulation of a compound of interest as described herein; a diluent solution; and instructions for the use of such liquid solutions. In certain instances, said diluent solution is selected from water; water and alcohol; water and polyethylene glycol (PEG); water, alcohol and PEG. In certain instances, the diluent solution comprises alcohol, where alcohol is ethanol. In certain instances, the pH of the diluent has a pH of about pH 7.4 or greater. In certain instances, the diluent has a pH of about pH 7.4 or greater and is buffered. In certain instances, the buffer concentration is between about 1 mM and about 100 mM. In certain instances, the buffer concentration is less than about 15 mM. In certain instances, the buffer concentration is between about 5 mM and about 10 mM. In certain instances, the diluent has a pH of about pH 7.4 or greater and is buffered with a pharmaceutically acceptable buffer.

Another aspect of the invention relates to a vial of Glibenclamide powder (micronized or non micronized) packaged with a vial of diluent, where the diluent has a pH of about pH 7.4 or greater and is buffered with a buffer selected from meglumine and diethanolamine. Certain other aspects of the invention relate to a vial of Glibenclamide powder (micronized or non micronized) packaged with a vial of diluent, where the diluent has a pH of about pH 7.4 or greater and is buffered with a buffer selected from meglumine and diethanolamine.

Another aspect of the invention relates to a glibenclamide powder (micronized or non micronized) comprising a buffer. Certain other aspects of the invention relate to a glibenclamide powder (micronized or non micronized) comprising a buffer and including a substantially pharmaceutically inert compound. In certain instances, the substantially pharmaceutically inert compound is selected from a sugar and a salt. In certain instances, the substantially pharmaceutically inert compound is selected from glucose, fructose, trehalose, sucrose, mannose, galactose, mannitol, sorbitol, sodium chloride, and potassium chloride.

Another aspect of the invention relates to a glibenclamide powder (micronized or non micronized) comprising a buffer and including another pharmaceutically active compound. In certain instances, the other pharmaceutically active compound is selected from 4-trans-hydroxy-glibenclamide, 3-cis-hydroxy-glibenclamide, tolbutamide, chlorpropamide, tolazamide, repaglinide, nateglinide, meglitinide, midaglizole, tolazamide, gliquidone, LY397364, LY389382, glyclazide, glimepiride, estrogen, estradiol, estrone, estriol, genistein, diethystilbestrol, coumestrol, zearalenone, non-steroidal estrogens, phytoestrogens, pinkolant, flufenamic acid, mefanamic acid, niflumic acid, rimonabant, and SKF 9635. In certain instances, the other pharmaceutically active compound is selected from 4-trans-hydroxy-glibenclamide, 3-cis-hydroxy-glibenclamide, tolbutamide, repaglinide, nateglinide, meglitinide, midaglizole, LY397364, LY389382, glyclazide, and glimepiride. In certain instances, the other pharmaceutically active compound is selected from pinkolant, flufenamic acid, mefanamic acid, niflumic acid, rimonabant, and SKF 9635. In certain instances, the other pharmaceutically active compound is selected from estrogen, estradiol, estrone, estriol, genistein, diethystilbestrol, coumestrol, zearalenone, non-steroidal estrogens, and phytoestrogens.

Another aspect of the invention relates to a vial containing lyophilized glibenclamide, a bulking agent, and a pH adjuster. Certain other aspects of the invention relate to a vial containing lyophilized glibenclamide, a bulking agent, and a pH adjuster, wherein the pH is adjusted using NaOH. Still other aspects of the invention relate to a vial containing lyophilized glibenclamide, a bulking agent, and a pH adjuster, wherein the concentration of glibenclamide is about 1 mg/mL. In certain instances, the bulking agent is mannitol. In certain instances, the pH prior to lyophilization is about pH 11.4. In certain instances, the starting material is micronized glibenclamide. In certain instances, packaged with a vial of diluent (buffered or not) with a pH of 7.4-8.0 to add to the product above following reconstitution to reduce pH.

Definitions

To facilitate an understanding of the present invention, a number of terms and phrases are defined below.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to standard pharmaceutical carriers, such as saline solution, water, emulsions (e.g., such as an oil/water or water/oil emulsions), and various types of wetting agents. The compositions can, in certain instances, include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable basic salt" refers to any pharmaceutically acceptable basic salts of a compound of the present invention which, upon administration to a subject, is capable of providing a compound of this invention or an active metabolite or residue thereof. As is known to those of skill in the art, "salts" of the compounds of the present invention may be derived from inorganic or organic bases. Examples of bases include, but are not limited to, alkali metals (e.g., sodium and potassium) hydroxides, alkaline earth metals (e.g., magnesium), hydroxides, ammonia, and compounds of formula $NW_4^+$, wherein W is $C_{1-4}$ alkyl, and the like.

EXAMPLES

The invention now being generally described, will be more readily understood by reference to the following examples, which are included merely for purposes of illustration of certain aspects and embodiments of the present invention, and are not intended to limit the invention.

Example 1

Lyophilized Glibenclamide

TABLE 3

|  | Low concentration formulation | High concentration formulation |
| --- | --- | --- |
| Concentration of glibenclamide | 0.2 mg/mL (0.1 mg/mL for NaCl bulking agent) (0.05 to 0.4 mg/mL) | 1.0 mg/mL (0.4 to 8 mg/mL) |
| pH prior to lyophilization | 9.4 (7+) | 11.4 (11+) |
| Bulking agents | Lactose (NaCl, Sucrose, Mannitol, Trehalose) | Mannitol (Sucrose, Lactose, Trehalose. No NaCl) |
| Bulking agent w/v % | 2% (1%+) | 3% (1%+) |
| pH Adjustments | Begin compounding by raising pH to 11.3 using NaOH, add glibenclamide and excipients, adjusting up to pH 11.3 regularly. Then reduce to 9.4 with HCl | Begin compounding by raising pH to 11.3 using NaOH, add glibenclamide and excipients, adjusting up to pH 11.3 regularly. No HCl. |
| Buffer | No buffer (or can be lightly buffered, e.g., 2 mM) | No buffer (or can be lightly buffered, e.g., 2 mM) |
| Reconstitute | WFI (water for injection) | WFI |
| pH after reconstitution | 8.4 to 9.4 (can drop as low as 7 and still reconstitute) | 10 to 11.4 |
| Dilution for bolus | Dilute 1:1 with 0.9% Saline (1:1+) | Dilute 1:10 with 0.9% Saline (1:1+) |
| Dilution for infusion | Further dilute until pH < 8.0, i.e., physiologically suitable. | Further dilute until pH < 8.0, i.e., physiologically suitable. |
| Solvents | None (or PEG or alcohol) | None (or PEG or alcohol) |
| Variations tried successfully | 0.25 mg/mL, pH 9.5 and pH 10.5 0.20 mg/mL, pH 9.5 and pH 10.5 0.1 mg/mL, pH 9.5 and pH 10.5 | 0.5 mg/mL, pH 11.3 |

Key: ranges or alternatives are shown in parenthesis. "Water for injection" includes purified, sterilized, filtered, and other water that is suitable and safe for administration to a patient.

Example 2A

Solubility Studies Using Micronized Glibenclamide Sucrose

Micronized glibenclamide in 2% sucrose (as a proxy for glucose, fructose, mannose, galactose, mannitol, sorbitol, lactose, trehalose, and other sugars, including mono-saccharides, di-saccharides) in water was prepared, as recorded in the left-hand column of Table 4. In addition, micronized glibenclamide was prepared in water without a bulking agent (see Table 4, right column). These were unbuffered solutions, so that 1) pH was adjusted to the target value, then 2) glibenclamide was added (which lowered the pH) and then 3) pH was re-adjusted up to the target. This was done iteratively until the pH was stable.

TABLE 4

| Solutions of Glibenclamide (GLB). | | | |
| --- | --- | --- | --- |
| Sucrose | | Water | |
| pH | GLB mg/ml | pH | GLB mg/ml |
| 7.45 | 0.051 | 7.36 | 0.019 |
| 7.50 | 0.099 | 7.55 | 0.096 |
| 8.24 | 0.310 | 8.65 | 0.799 |
| 8.66 | 1.069 | 8.73 | 0.087 |
| 9.16 | 2.608 | 9.13 | 0.205 |
| 9.53 | 3.060 | 9.57 | 3.968 |
| 9.74 | 4.103 | 10.28 | 4.871 |

TABLE 4-continued

Solutions of Glibenclamide (GLB).

| Sucrose | | Water | |
|---|---|---|---|
| pH | GLB mg/ml | pH | GLB mg/ml |
| 11.30 | 3.416 | 11.19 | 4.673 |
| 11.23 | 3.811 | 11.44 | 4.841 |
| 11.99 | 1.904 | 12.27 | 2.513 |

Glibenclamide concentration (shown in units of mg/mL on the vertical axis) is plotted in FIG. 1 as a function of pH in an aqueous sucrose solution (2% sucrose in water, where "%" means g/100 mL) and in water alone.

The results for lactose and mannitol and other sugars (e.g., glucose, fructose, mannose, galactose, trehalose, sorbitol, and other sugars, including mono-saccharides, di-saccharides) is contemplated to be similar to those shown for sucrose.

Saline

Micronized glibenclamide in 2% saline and in 0.9% saline in water was prepared and analyzed (see Table 5). These solutions were unbuffered solutions, so the following method was used: 1) pH was adjusted to the target, then 2) glibenclamide was added (which lowered the pH) and then 3) pH was re-adjusted up to the target. This was done iteratively until pH was stable. "GLB" indicates glibenclamide.

TABLE 5

Solutions of Glibenclamide (GLB).

| Saline 2% | | Saline 0.9% | |
|---|---|---|---|
| pH | GLB mg/ml | pH | GLB mg/ml |
| 7.24 | 0.012 | | |
| 7.97 | 0.028 | | |
| 8.34 | 0.087 | 8.070 | 0.024 |
| 8.89 | 0.214 | 8.440 | 0.109 |
| 8.94 | 0.233 | 9.180 | 0.435 |
| 9.49 | 0.205 | 9.920 | 0.420 |
| 10.31 | 0.215 | 10.480 | 0.456 |
| 10.98 | 0.192 | 11.060 | 0.445 |
| 11.49 | 0.194 | 11.610 | 0.538 |
| 12.10 | 0.216 | 12.070 | 0.476 |

Figure 2:
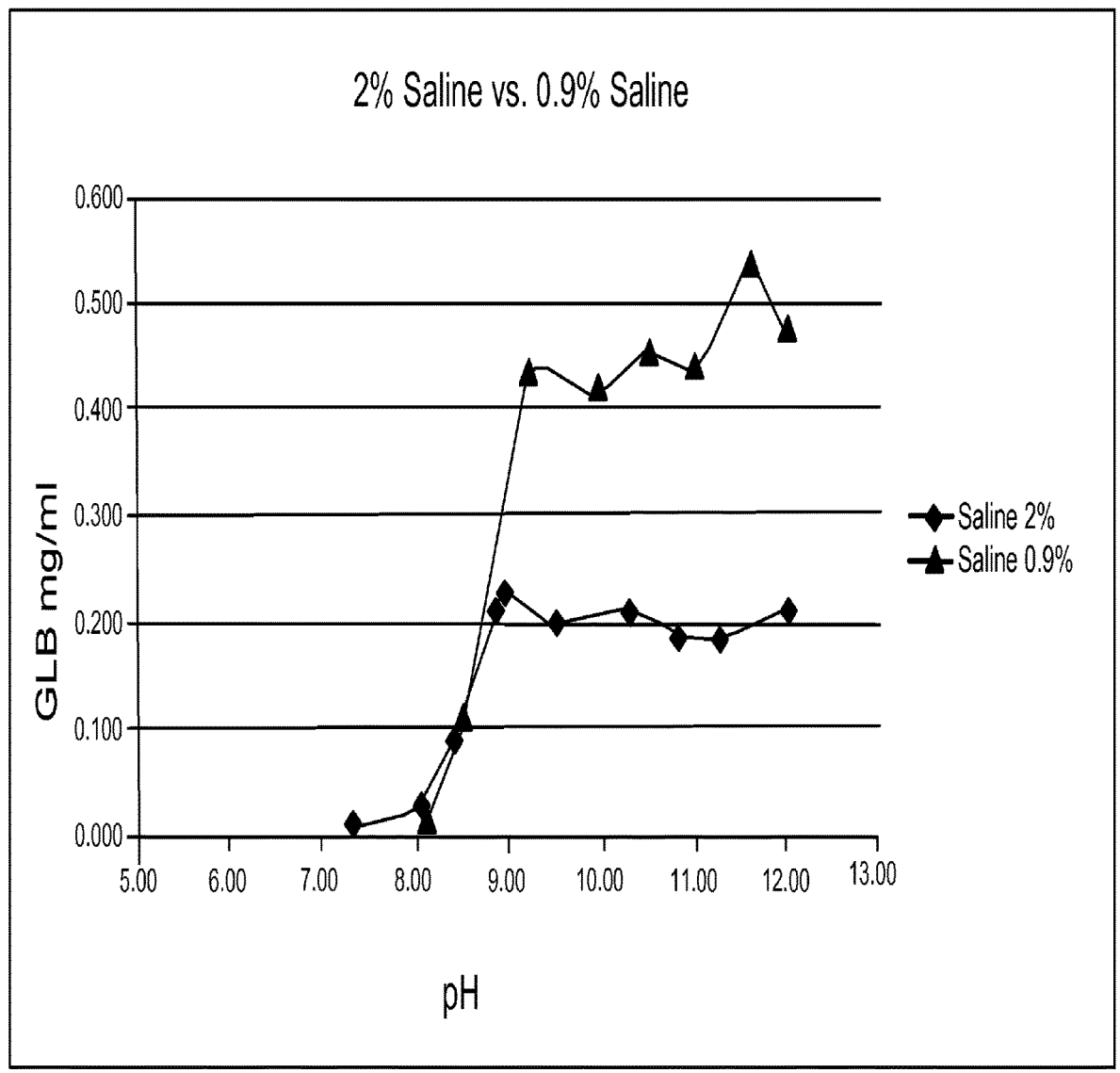
FIG. 2 shows the amount of glibenclamide in solution (in mg/mL) at various pH values, plotted with glibenclamide amounts on the vertical axis, and pH shown as increasing from left to right along the horizontal axis.
Figure 3:
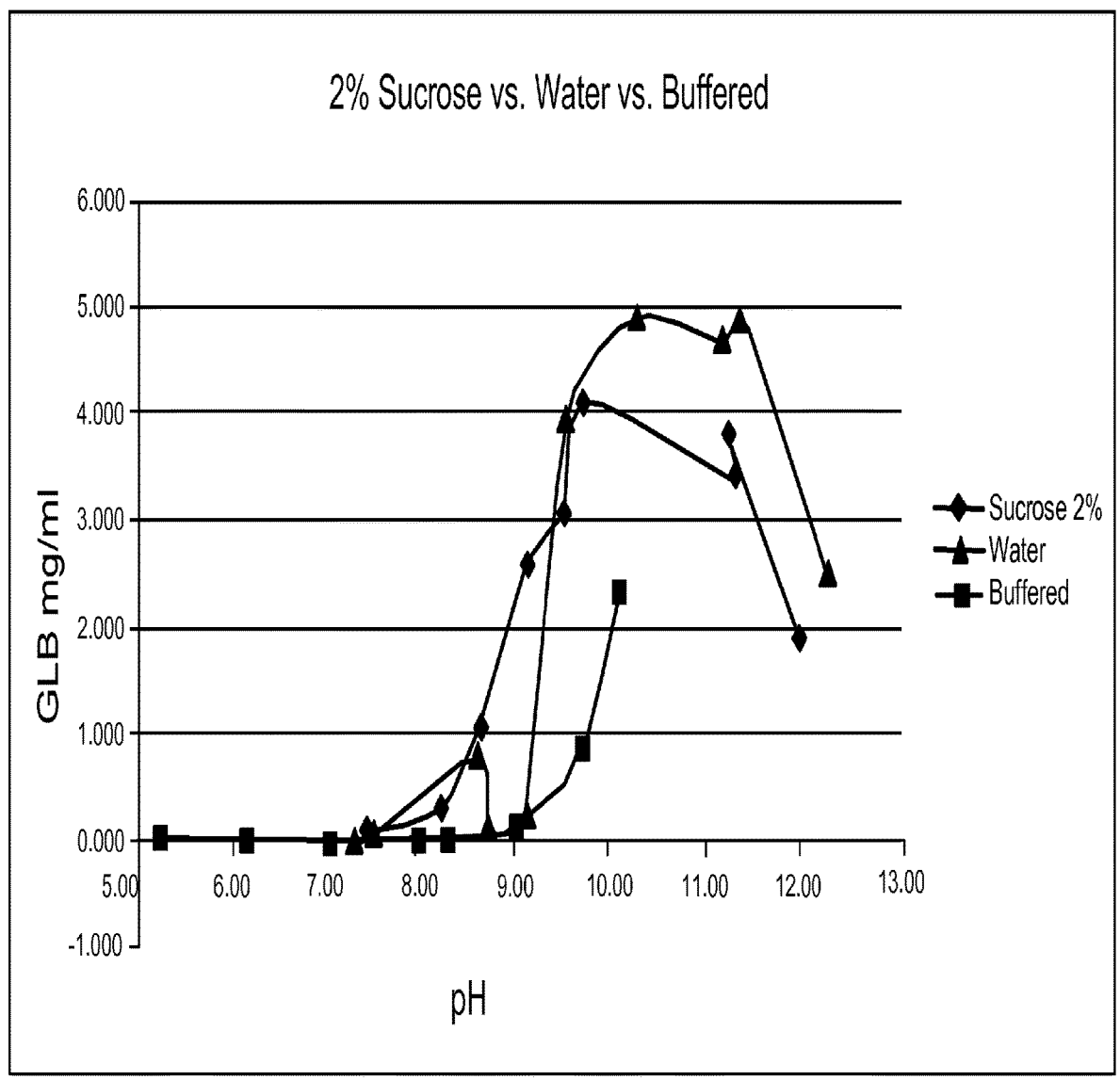
FIG. 3 shows the amount of glibenclamide in solution (in mg/mL) in saline, sucrose, and buffered (Britton Robinson) water solutions at various pH values, plotted with glibenclamide amounts on the vertical axis, and pH shown as increasing from left to right along the horizontal axis.

The amount of glibenclamide (in mg/mL) was plotted on the vertical axis in FIG. 2 as a function of pH (along the horizontal axis) for solutions of glibenclamide in saline solutions in and in water.

As can be seen in FIG. 2, the solubility of glibenclamide was less is saline solutions, with higher concentrations of NaCl further reducing the solubility of glibenclamide. That is, the maximal amounts of glibenclamide in the 0.9% saline solution were greater than the maximal amounts of glibenclamide in the 2% saline solution.

Buffered Solutions

Buffered water solutions (Britton Robinson buffers) were used to determine the amounts of glibenclamide soluble in buffered solutions without added salt or added sugar.

Experiments using buffered water plus glibenclamide resulted in the following concentrations by pH:

TABLE 6

Buffered (Britton Robinson)

| pH | GLB mg/mL |
|---|---|
| 5.3 | 0.01 |
| 6.200 | 0.01 |
| 7.100 | 0.01 |
| 8.000 | 0.02 |
| 8.3 | 0.02 |
| 9.000 | 0.14 |
| 9.700 | 0.85 |
| 10.100 | 2.35 |

When compared with the 2% sucrose and water-only versions, it appears that the solubility is slightly shifted in the buffered version, and that higher solubility can be achieved using NaOH adjustment without buffering:

Solution Containing 3% Mannitol, 1 mg/mL Glibenclamide, and Having a pH of 11.3

Glibenclamide—Trial Formulations (JC No.: R08-02682) and Lyophilization and Reconstitution (JC.: R08-02683)

Experimental Details

Two bulk solutions of Glibenclamide in deionized water (Formula A, 1 mg/mL; Formula B, 0.5 mg/mL) were prepared, both with 3% mannitol. Dilutions were prepared from each bulk solution. The bulk solutions were assessed for appearance and pH immediately after preparation (0 hours), and after 5 (bulk solutions only) and 24 hours. Ten vials were filled from each of the two bulk solutions and subsequently lyophilized. Two vials from each batch were reconstituted with deionized water and assessed for appearance and pH. In the following, note that dilutions were made using 0.9% saline solution.

The results are summarized below:

Results and Discussion

BN 838-097 (Glibenclamide 1.0 mg/mL in 3% mannitol, pH 11.4) and BN 838-099

(Glibenclamide 0.01 mg/mL (1:99 Dilution of BN 838-097))

| | | Time + Initial (0 hours) | |
|---|---|---|---|
| Experiment No. | Dilution | Appearance | pH |
| 838-097 | Undiluted | Clear colourless solution | 11.5 |
| 838-099 | 1.99 | Clear colourless solution | 6.5 |

| | | Time = 5 hours | |
|---|---|---|---|
| Experiment No. | Dilution | Appearance | pH |
| 838-097 | Undiluted | Clear colourless solution | 11.4 |

| | | Time = 24 hours | |
|---|---|---|---|
| Experiment No. | Dilution | Appearance | pH |
| 838-097 | Undiluted | Clear colourless solution | 11.4 |
| 838-099 | 1.99 | Clear colourless solution | 6.7 |

Samples assessed at 0, 5 and 24 hours were clear colourless solutions with no precipitate. The pH of the undiluted and diluted samples were stable over 24 hours.

BN 838-101 (Glibenclamide 0.5 mg/mL in 3% mannitol, pH 11.4), BN 838-103 (Glibenclamide 0.01 mg/mL (1:49 Dilution of BN 838-101)), and BN 838-105 (0.003 mg/mL (1:2 Dilution of BN 838-103))

The pH on dilution of BN 838-101 was noted to be above pH 8 (BN 838-103), therefore a further 1:2 dilution was done of BN 838-103 (therefore BN 838-105).

Time Zero

| Experiment No. | Dilution | Time = Initial (0 hours) Appearance | pH |
|---|---|---|---|
| 838-101 | Undiluted | Clear colourless solution | 11.4 |
| 838-103 | 1:49 | Clear colourless solution | 9.4 |
| 838-105 | 1:2 (of BN 838-103) | Clear, colourless solution | 6.5 |

Time: 4 Hours

| Experiment No. | Dilution | Time = 4 hours Appearance | pH |
|---|---|---|---|
| 838-101 | Undiluted | Clear colourless solution | 11.4 |

Time: 24 Hours

| Experiment No. | Dilution | Time + Initial (0 hours) Appearance | pH |
|---|---|---|---|
| 838-101 | Undiluted | Clear colourless solution | 11.4 |
| 838-103 | 1:49 | Clear colourless solution | 8.4 |
| 838-105 | 1:2 (of BN 838-103) | Clear colourless solution | 7.5 |

Samples assessed at 0, 4 and 24 hours were clear colourless solutions with no precipitate. The pH of the undiluted sample was stable over 24 hours. The pH of the diluted sample (BN 838-103 (1:49 Dilution of BN 838-101)), showed a drop in pH by approximately 1 pH unit over 24 hours.

As described above, batch 838-103 was further diluted 1:2 due to the pH of batch 838-103 being above pH 8. The pH of this diluted sample increased by approximately 1 pH unit over 24 hours, but remained below pH 8.

Lyophilization and Reconstitution

| Experiment No. | Dilution | Appearance (n = 2) | pH (n = 2) |
|---|---|---|---|
| 838-097 | Undiluted | Clear colourless solution | 11.4, 11.4 |
| 838-101 | Undiluted | Clear colourless solution | 11.4, 11.4 |

As described above, vials were filled from each of the bulk solutions above and lyophilized. At the end of the drying cycle, the vials were unloaded from the dryer, and 2 vials from each batch reconstituted with deionized water.

The freeze dried cakes dissolved very rapidly upon addition of deionized water to give clear colourless solutions with no precipitate. The pH was measured and found to be 11.4 for both batches. A similar exercise was undertaken at another laboratory, and the resultant pH following reconstitution of the lyophilized material was 10.7. Therefore, these results indicate that the formulations can be successfully lyophilized.

Example 2B

EXEMPLARY FORMULATION: Glibenclamide (1 mg/mL), NaOH, and water; the formulation having a pH of 11.3.

TABLE 7

| API (active pharmaceutical ingredient) | Micronized Glibenclamide (Cambrex) |
|---|---|
| API Concentration | 1.0 mg/mL |
| pH | 11.4 ± 0.1 |
| pH adjustment | NaOH |
| Bulking Agent | Mannitol |
| Bulking Agent % | 3% |
| Water | WFI (water for injection) |
| Specific Exclusions | No HCl |

Preparation

Lyophilized glibenclamide was produced by the following method:
1. Adjusted 95 mL WFI to pH 11.4±0.1 using 0.2M sodium hydroxide solution, while stirring at medium speed.
2. Add mannitol and glibenclamide with continued stirring. Adjust pH to 11.4±0.1.
3. During stirring, adjust pH of solution to 11.4 using 0.2M sodium hydroxide solution every few minutes. Time taken for glibenclamide to go into solution is approximately 30 minutes.
4. Add WFI to bring volume to 100 mL.
5. Adjust pH to 11.4 if required.
6. The solution of step 5 is lyophilized. A white or off-white cake is formed. The lyophilized material has a sufficiently large surface area that there is no need to further grind it.

Note: No HCl is used. Glibenclamide causes some lowering of the pH; no further reduction in pH is needed.

However, if desired, a further, optional, grinding step after step 6 may be performed to grind the lyophilized cake into a micronized powder. Such a grinding step may be useful, for example, with large amounts of lyophilate, and may be omitted in any case, and particularly where the cake is small in size, within a vial, or for any other reason.

In experiments performed by the applicant, micronized glibenclamide was obtained from Cambrex (supplied in micronized form; obtained from Cambrex Profarmaco Milano, Sri, Via Curiel, 34, 20067 Paullo (Mich.), Italy, a division of Cambrex Corporation of East Rutherford, N.J. 07073). This micronized glibenclamide was then put into solution, and that solution was then lyophilized according to the methods disclosed herein.

Unbuffered Solutions and Formulations

Unbuffered solutions and formulations were prepared—that is, the solutions or formulations lacking a buffer. However, it is contemplated that solutions and formulations containing only low concentrations of buffer (e.g., less than about 2 mM) or only weak buffers or buffers with low buffering capacity, so that the solution pH was not well-regulated, if regulated at all, by a buffer, are amenable to the present solutions and formulations.

In certain embodiments of the methods disclosed herein, solution pH is to be continually increased during the manufacturing process as more glibenclamide goes into solution.

Even though the pH is high following reconstitution, when the reconstituted solution is diluted in 0.9% Saline (e.g., diluted 50 times to about 100 times, for example), the pH comes down to physiologically acceptable levels. Thus, such reconstituted solutions, upon dilution, are suitable for use, for example, in a 3-day infusion. This suitability is surprising due to the lack of buffering, which allows the pH to fall to acceptable levels upon dilution in a physiologically acceptable solution, without further effort on the part of those diluting the solution.

No HCl (Hydrochloric Acid)

Use of NaOH to increase pH, together with use of HCl to reduce pH can reduce the collapse temperature during lyophilization. Accordingly, it is preferable to use only NaOH for pH adjustment. Thus, in certain embodiments, HCl is not used: i.e., there is no use of HCl to adjust the pH of a solution or formulation for lyophilization.

No PEG (Polyethylene Glycol) or Other Organic Solvent

Unlike other examples of lyophilized glibenclamide in the art, the use organic solvents is not required in the methods and compositions disclosed herein. The absence of organic solvents is believed to be an advantage over prior art formulations, and may simplify the FDA regulatory pathway (e.g., simplify the efforts needed to obtain regulatory approval for the use of solutions, formulations, lyophilates, etc., according to the methods disclosed herein, for use in treating patients and in producing medicaments for the treatment of diseases and conditions of patients) and so allow for rapid adoption of these methods in clinical applications.

Relationship Between Starting pH, Starting Concentration, Total Dose, and Maximum Infusible Volume Per Day For a particular starting concentration (e.g., 0.5 mg/mL), the starting pH that is high enough to maintain that concentration (e.g., pH 11.3) and total intended dose (e.g., 3 mg per day), the maximum infusible volume per day (e.g., 1,000 mL) has to be sufficiently high that when the drug is diluted in 0.9% Saline to get to the maximum infusible volume per day, the dilution ratio (994:6, i.e., 166:1) is higher than the minimum dilution ratio required to reach a pH of less than or equal to pH 8.5 or most preferentially pH 7.0 (in this case, the minimum dilution ratio is somewhere between 50-100 based on the experiments discussed above).

Example 3

Exemplary Formulation: Glibenclamide (0.2 mg/mL), NaOH, HCl, and Water; the Formulation Having a pH of 9.4.

This formulation is prepared as described for the 1 mg/mL glibenclamide formulation of Example 2B except that HCl is used as final step before lyophilization to reduce the pH to 9.4.

Example 4

Exemplary Formulation: Glibenclamide (0.1 mg/mL), NaOH, HO, and Saline; the Formulation Having a pH of 9.4.

This formulation is prepared as described for the 1 mg/mL glibenclamide formulation of Example 2B except that HCl is used as final step before lyophilization to reduce the pH to 9.4.

In addition, this formulation, and others of similar concentration, is immediately isotonic upon reconstitution and contains no carbohydrates, which is believed to provide a clinical advantage in treating stroke patients, for example, as clinicians are often not comfortable giving carbohydrates to stroke patients who are often hyperglycemic.

Freeze-Drying (Lyophilization)

Freeze drying (also known as lyophilization) is a process in which a material is first frozen, and then dried by sublimation (by reducing the air pressure around the frozen solid) and adding enough heat to cause the frozen water in the material to sublime directly from the solid phase to gas, leaving a dried material. Lyophilates often appear as dry flakes or other particles, which may then be further broken into smaller particles to form, for example, a powder. A thorough description of lyophilization is found in the book *Lyophilization—Introduction and Basic Principles* by Thomas Jennings (published by CRC Press LLC, Boca Raton, Fla., USA (1999), ISBN: 9781574910810 and ISBN-10: 574910817).

The freeze-drying process may be thought of as including three steps: Freezing, Primary Drying, and Secondary Drying.

The first step, freezing, is, as its name implies, simply the process of freezing the material. The material should be cooled to a temperature below the eutectic point (the lowest temperature at which the solid and liquid phase of the material coexist) of the material to freeze it and to insure that sublimation rather than melting will occur with subsequent heating of the frozen material under vacuum or low pressure. Since the eutectic point occurs at the lowest temperature where the solid and liquid phase of the material can coexist, freezing the material at a temperature below this point ensures that sublimation rather than melting will occur in the following steps. Cooling of amorphous (glassy) materials (which lack a eutectic point) should be to below the critical temperature of the material.

For example, a material may be frozen in a freeze-drying flask cooled by any suitable method (e.g., refrigeration, placement in a bath of dry ice and methanol, or placement in a liquid nitrogen bath).

In the initial drying step (the primary drying phase) the pressure is lowered and enough heat is supplied for the frozen water in the material to sublimate. Most of the water is removed in this initial drying phase. In this phase, pressure is controlled through the application of partial vacuum to speed sublimation.

Following the initial drying phase, further drying (the secondary drying phase) is done by raising the temperature higher than the temperature used in the primary drying phase. The secondary drying phase may remove water that has condensed or moved from an initial location during the primary drying phase. Low pressure is typically used in this phase as well.

Lyophilized products are often very stable, particularly if measures are taken to prevent reabsorption of water. For example, lyophilization is useful for providing pharmaceuticals that may be stored for many years. However, when needed, lyophilized materials products can be readily rehydrated (reconstituted) as the process produces many microscopic pores in the material that aid reintroduction of water. Lyophilized material can be easily stored, shipped and later reconstituted to its original form for injection.

Micronizing Reduction of the average particle size of a granulated or powdered solid may be termed micronization, that is, for example, reducing the drug's particle size or micronizing the drug to have an average particle size of a few microns. It is often found that dosage forms which contain micronized drug particles exhibit enhanced solubility and consequently an increase in the bioavailability of the drugs.

Traditionally, dry materials were ground into fine powders (micronized) by hand by action of a mortar and pestle, in which the material was crushed into finer and finer particles between the hard pestle and the hard mortar. Many mechanized micronization techniques (e.g., milling and grinding)

use friction to reduce particle size. A typical industrial mill is composed of a cylindrical metallic drum that contains grinding elements (e.g. steel spheres). As the drum rotates the grinding elements inside the drum collide with the particles of the solid, and, when trapped between two grinding elements, the particles are crushed to produce smaller particles having smaller diameters. Alternatively, grinding wheels or other grinding elements may be used to micronize particles, such as powders or flakes, into smaller particles.

Methods like crushing and cutting are also used for reducing particle diameter, but produce rougher particles compared to milling and grinding (and are therefore the early stages of the micronization process). Crushing employs hammer-like tools to break the solid into smaller particles by means of impact. Cutting uses sharp blades to cut the rough solid pieces into smaller ones.

The micronization of solid materials, including proteins and drugs, to form solid particles suitable for micro encapsulation (e.g., particles having an average particle size less than about less than 20 µm, or less than about 10 µm) has been achieved using a variety of approaches including milling, as discussed above, and by spray-drying, spray freeze-drying, and supercritical anti-solvent (SAS) precipitation techniques as well.

Various milling techniques are known. For example, in U.S. Pat. No. 5,952,008 to Backstrom et al. jet milling is used to produce particles smaller than 10 µm for inhalation administration. U.S. Pat. No. 5,354,562 to Platz et al. discloses solid particle aerosol formulations of polypeptide drugs made by lyophilizing solutions of the drugs which contain milling stabilizers that inhibit degradation of the drug during subsequent milling. The lyophilized drug is milled in fluid energy mills that have been fitted with abrasion resistant materials. The resulting particles are between 0.5 to 4 µm when milled at high pressure and between 4 µm to 15 µm when milled at low pressure. U.S. Pat. No. 5,747,002 to Clark et al. discloses jet milling of sodium chloride to produce particles with a size distribution smaller than 7 µm.

U.S. Pat. No. 5,817,343 to Burke discloses a method for forming polymer/drug microparticles by forming a polymer solution/insoluble drug mixture; removing solvent from the mixture to form a hard matrix containing the drug particles in polymer; and micronizing the matrix by fragmenting (e.g., grinding or milling) the matrix below the glass-transition point of the polymer.

Sonication is another technique employed to micronize particles. For example, U.S. Pat. No. 4,384,975 to Fong et al. discloses the preparation of microspheres by solvent removal using sodium oleate as the emulsifier. Micronization of core material by milling or ultrasonic probe sonication of solid drug particles in polymer solution is disclosed. Tracy, Biotechnol. Prog, 14:108 15 (1998) discloses atomizing growth hormone in solution using an ultrasonic nozzle, freezing the dispersed droplets in a slurry of frozen ethanol, and then lyophilizing to remove the non-solvent and harden the droplets. The resulting hollow spheres are further micronized by ultrasonic probe treatment to fragment the spheres, which fragments are then encapsulated.

Example 5

Water Formulations for Preparing Lyophilized Tolbutamide

Tolbutamide is 24 times more soluble in water than glibenclamide (109 mg/L vs. 4 mg/L) and so is more easily used in water solutions. However, about 100 times as much tolbutamide as glibenclamide is needed to have the same clinical effect as glibenclamide. Thus, although in some embodiments, similar amounts of tolbutamide as glibenclamide may be included in the formulations and lyophilates having features of the invention, or greater tolbutamide (or other drugs, as desired, including for example, repaglinide, nateglinide, meglitinide, midaglizole, LY397364, LY389382, glyclazide, glimepiride and other drugs or metabolites of drugs which interact with SURs; may include ion channel blockers such as, for example, pinkolant, flufenamic acid, mefanamic acid, niflumic acid, rimonabant, and SKF 9635; may include estrogen, estradiol, estrone, estriol, genistein, diethystilbestrol, coumestrol, zearalenone, non-steroidal estrogens, phytoestrogens or other steroid compound) are included as compared to the amounts of glibenclamide discussed above.

In addition, formulations may include mixtures of drugs (e.g., glibenclamide plus pinkolant; or glibenclamide plus flufenamic acid; or glibenclamide plus mefanamic acid; or glibenclamide plus niflumic acid; or glibenclamide plus rimonabant; or glibenclamide plus SKF 9635; or glibenclamide plus estrogen; or glibenclamide plus estradiol; or glibenclamide plus estrone; or glibenclamide plus estriol; or glibenclamide plus genistein; or glibenclamide plus diethystilbestrol; or glibenclamide plus coumestrol; or glibenclamide plus zearalenone; or glibenclamide plus a non-steroidal estrogen; or glibenclamide plus a phytoestrogen; or glibenclamide plus another drug or metabolite of a drug which interacts with SURs).

TABLE 8

Tolbutamide Formulations.

| | Low Concentration formulation | High concentration formulation |
|---|---|---|
| Concentration of Tolbutamide | 0.2 mg/mL (0.1 mg/mL for NaCl bulking agent) (0.05 to 0.4 mg/mL) | 1.0 mg/mL (0.4 to 8 mg/mL) |
| pH prior to lyophilization | expected to be 9-10 | expected to be 11 or more |
| Bulking agents | Lactose (or NaCl, Sucrose, Mannitol, or Trehalose) | Mannitol (or Sucrose, Lactose, or Trehalose. No NaCl) |
| Bulking agent w/v % | 2% to 3% | 3% to 4% |

TABLE 8-continued

Tolbutamide Formulations.

|  | Low Concentration formulation | High concentration formulation |
|---|---|---|
| pH Adjustments | Begin compounding by raising pH to pH 11 or above using NaOH, add tolbutamide and excipients, adjusting up to pH 11 regularly. Then reduce to 9-10 with HCl. | Begin compounding by raising pH to 11 or above using NaOH, add tolbutamide and excipients, adjusting up to pH 11 regularly as necessary. No HCl added. |
| Buffer | No buffer (or the solution can be lightly buffered, e.g., 2 mM) | No buffer (or the solution can be lightly buffered, e.g., 2 mM) |
| Reconstitute pH after reconstitution | WFI (water for injection) expected to be 8 to 9 (can reduce pH to 7 and still reconstitute) | WFI expected to be 10 to 12 |
| Dilution for bolus | Dilute 1:1 or greater with 0.9% Saline | Dilute 1:10 or greater with 0.9% Saline |
| Dilution for infusion | Further dilute until pH < 8.0, i.e., physiologically suitable. | Further dilute until pH < 8.0, i.e., physiologically suitable. |
| Solvents | None (or an alcohol or polyethylene glycol) | None (or an alcohol or polyethylene glycol) |

Key: ranges or alternatives are shown in parenthesis.

Similar to the glibenclamide solutions, formulations, and lyophilates discussed above, tolbutamide solutions, formulations, and lyophilates may be prepared. Such tolbutamide solutions and formulations may be water solutions of tolbutamide, without sugars, salts, or buffers; may be water solutions of tolbutamide also including a sugar (e.g., one or more of glucose, fructose, mannose, galactose, mannitol, sorbitol, lactose, trehalose, sucrose, and other sugars, including mono-saccharides, di-saccharides, and other sugars), may be water solutions of tolbutamide also including a salt (e.g., sodium chloride or potassium chloride), may be water solutions of tolbutamide also including a buffer (e.g., a Britton-Robinson buffer, a phosphate buffer, a "Tris" buffer (containing Tris(hydroxymethyl)aminomethane), a HEPES buffer (containing N-(2-Hydroxyethyl)piperazine-N'-(2-ethanesulfonic acid), or other buffer). It will be understood that such solutions, formulations, and lyophilates made from such solutions and formulations, may include combinations of the above.

Example 6

Water Formulations for Preparing Lyophilized Repaglinide

Repaglinide is another pharmaceutically active ingredient that acts on SURs and is suitable for the practice of the invention. Repaglinide has a water solubility of 0.6 mg/mL at pH 9, which is a bit lower than the solubility of glibenclamide in water at this pH. Accordingly, repaglinide water formulations are contemplated to be similar to glibenclamide water formulations.

TABLE 9

Repaglinide Formulations.

|  | Low ConcentrationFormulation | High concentration formulation |
|---|---|---|
| Concentration of repaglinide | 0.2 mg/mL (0.1 mg/mL for NaCl bulking agent) (or 0.05 to 0.4 mg/mL) | 1.0 mg/mL (or 0.4 to 8 mg/mL) |
| pH prior to lyophilization | expected to be 9-10 | expected to be 11 or more |
| Bulking agents | Lactose (or NaCl, Sucrose, Mannitol, or Trehalose) | Mannitol (or Sucrose, Lactose, or Trehalose. No NaCl) |
| Bulking agent % | 2% to 3% | 3% to 4% |
| pH Adjustments | Begin compounding by raising pH to pH 11 or above using NaOH, add repaglinide and excipients, adjusting up to pH 11 regularly. Then reduce to 9-10 with HCl | Begin compounding by raising pH to 11 or above using NaOH, add repaglinide and excipients, adjusting up to pH 11 regularly as necessary. No HCl added. |
| Buffer | No buffer (can be lightly buffered e.g. 2 mM) | No buffer (can be lightly buffered e.g. 2 mM) |
| Reconstitute pH after reconstitution | WFI (water for injection) expected to be 8 to 9 (can drop as low as 7 and still reconstitute) | WFI expected to be 10 to 12 |

TABLE 9-continued

Repaglinide Formulations.

| | Low Concentration Formulation | High concentration formulation |
|---|---|---|
| Dilution for bolus | Dilute 1:1 or greater with 0.9% Saline | Dilute 1:10 or greater with 0.9% Saline |
| Dilution for infusion | Further dilute until pH < 8.0 i.e. physiologically suitable. | Further dilute until pH < 8.0 i.e. physiologically suitable. |
| Solvents | None (or PEG or alcohol) | None (or PEG or alcohol) |

Key: ranges or alternatives are shown in parenthesis.

Similarly to the glibenclamide and tolbutamide solutions, formulations, and lyophilates discussed above, repaglinide solutions, formulations, and lyophilates may be prepared. Such repaglinide solutions and formulations may be water solutions of repaglinide, without sugars, salts, or buffers; may be water solutions of repaglinide also including a sugar (e.g., one or more of glucose, fructose, mannose, galactose, mannitol, sorbitol, lactose, trehalose, sucrose, and other sugars, including mono-saccharides, di-saccharides, and other sugars), may be water solutions of repaglinide also including a salt (e.g., sodium chloride or potassium chloride), may be water solutions of repaglinide also including a buffer (e.g., a Britton-Robinson buffer, a phosphate buffer, a "Tris" buffer (containing Tris(hydroxymethyl)aminomethane), a HEPES buffer (containing N-(2-Hydroxyethyl)piperazine-N'-(2-ethanesulfonic acid), or other buffer). It will be understood that such solutions, formulations, and lyophilates made from such solutions and formulations, may include combinations of the above.

Similarly, solutions and formulations, and lyophilates made from such solutions and formulations, may be made from other drugs and pharmaceutically active compounds and ingredients. Thus, for example, similar solutions and formulations, and lyophilates made from such solutions and formulations, may be made from, e.g., nateglinide, meglitinide, midaglizole, LY397364, LY389382, glyclazide, glimepiride and other drugs or metabolites of drugs which interact with SURs; ion channel blockers such as, for example, pinkolant, flufenamic acid, mefanamic acid, niflumic acid, rimonabant, and SKF 9635; estrogen, estradiol, estrone, estriol, genistein, diethystilbestrol, coumestrol, zearalenone, non-steroidal estrogens, phytoestrogens or other steroid compound; or other pharmaceutically active compound.

Kits may be prepared including solutions, formulations, and lyophilates having features of the invention. For example, a kit may include a liquid formulation of a compound of interest (e.g., as discussed above, including, for example, glibenclamide, tolbutamide, repaglinide, nateglinide, meglitinide, midaglizole, LY397364, LY389382, glyclazide, glimepiride and other drugs or metabolites of drugs which interact with SURs; ion channel blockers such as, for example, pinkolant, flufenamic acid, mefanamic acid, niflumic acid, rimonabant, and SKF 9635; estrogen, estradiol, estrone, estriol, genistein, diethystilbestrol, coumestrol, zearalenone, non-steroidal estrogens, phytoestrogens or other steroid compound; or other pharmaceutically active compound; and instructions for the use of such liquid solutions. For example, the instructions may include methods and description as described above, including methods for providing water solutions containing an active pharmaceutical ingredient. In embodiments, the instructions may simply describe how one may add appropriate amounts of water to a dry lyophilate to provide a water solution. In embodiments, the instructions may further describe how one may measure the pH of such a solution, and may describe how one may adjust the pH of such a solution as desired or as appropriate, as described above. In embodiments, the instructions may describe how one may add appropriate further ingredients, including buffers, salts, excipients, extenders, or other ingredients, as described above, to such a solution. In embodiments, the instructions may describe how one may add such a solution to a suitable solution for injection, either as bolus or for infusion, as described above.

In further embodiments, a kit may include a lyophilized formulation of a compound of interest (e.g., as discussed above); a diluent solution; and instructions for the use of such liquid solutions. For example, such a diluent solution may be selected from water; water and alcohol (e.g., ethanol); water and polyethylene glycol (PEG); water, alcohol and PEG. In embodiments, the pH of the diluent may be a pH of about pH 7.4 or greater.

In further embodiments, the pH of the diluent is about pH 7.4 or greater and the diluent is buffered; the buffer may be a pharmaceutically acceptable buffer. In yet further embodiments, the diluent of the kit is buffered, and the buffer concentration is between about 1 mM and about 100 mM. In embodiments, the buffer concentration may be less than about 15 mM; and in embodiments, the buffer concentration is between about 5 mM and about 10 mM.

Example 7

Stability of Lyophilized Glibenclamide

A study was carried out to asses the stability of lyophilized glibenclamide to extended storage at various temperatures and relative humidity. The data obtained from this study indicate that lyophilized glibenclamide has good stability over at least 3 months at the temperatures and relative humidity conditions tested. Experimental procedures and results from the study are described in detail below.

Experimental Procedures: Vials containing lyophilized glibenclamide powder were used in this study. The lyophilized glibenclamide powder was obtained by lyophilization of an aqueous mixture containing 4.7-5.0 mg glibenclamide (The experiment started with 6 mg of glibenclamide, but some glibenclamide remained on the filter following filtration of the aqueous mixture. As a result, the filtrate used for lyophilization contained 4.7-5.0 mg of glibenclamide), 180 mg mannitol, and sodium hydroxide as needed to adjust the pH to11.3 prior to lyophilization. Lyophilization of this aqueous mixture removed 6 mL of water per vial.

The lyophilized glibenclamide powder was evaluated at the following time points for appearance, reconstitution time, p1-1 after reconstitution, moisture content, amount of glibenclamide as analyzed by HPLC, and the amount of substances related to glibenclamide:

Time=initial at 2-8° C.
Time=6 weeks at 2-8° C.
Time=6 weeks at 25° C. and 60% RH
Time=6 weeks at 40° C. and 75% RH
Time=6 weeks and 13 days at 25° C. and 60% RH
Time=6 weeks and 13 days at 40° C. and 75% RH
Time=3 months at 2-8° C.
Time=3 months at 25° C. and 60% RH
Time=3 months at 40° C. and 75% RH The analyses were carried out as follows:

Appearance and Particulates: Lyophilized vials were inspected visually (before and after reconstitution with 6 mL of water for injection).

Reconstitution Time: Reconstitution time of duplicate samples from 2 separate vials were measured after adding 6 mL of water for injection.

The pH of duplicate samples from two separate vials used for the reconstitution were measured.

Assay for Amount of Glibenclamide and Assay for Substances Related to Glibenclamide: The assay for glibenclamide in injection samples was determined by an isocratic HPLC method. A Zorbax XDB-C18, 5.0 vun, 150 mm×4.6 mm column was used, operated at 50° C., eluting with an acetonitrile/water/fonnic acid eluent. Methanol was used as diluent. The glibenclamide content was assayed by comparison with similarly chromatographed reference solutions. Related substances were evaluated as area % with reference to the Glibenclamide peak at 230 nm.

Moisture Content Analyzed by Coulometric Karl Fischer: The moisture content was evaluated by dispersing the lyophilized cake in benzyl alcohol and analyzing this solution by coulometric Karl Fischer titration. Results are reported as mg/vial.

The invention claimed is:

1. A method of forming a reconstituted pharmaceutical formulation, the method comprising reconstituting a lyophilized composition that comprises:
   a) glibenclamide or a pharmaceutically acceptable salt thereof;
   b) at least one substantially pharmaceutically inert compound selected from the group consisting of glucose, fructose, mannose, galactose, mannitol, sorbitol, lactose, trehalose, sucrose, sodium chloride and potassium chloride; and
   c) one or more alkali bases,
in deionized water at a concentration of about 0.2 mg/mL to about 1.0 mg/mL of the glibenclamide or a pharmaceutically acceptable salt thereof, and forming said reconstituted pharmaceutical formulation having a pH greater than 8,
   wherein the lyophilized composition is stable for at least 3 months at 25° C. and 60% relative humidity.

2. The method of claim 1, wherein the weight of the one or more of glucose, fructose, mannose, galactose, mannitol, sorbitol, lactose, trehalose, sucrose, sodium chloride, and potassium chloride is at least about 10 times the weight of glibenclamide or a pharmaceutically acceptable salt thereof in the lyophilized composition.

3. The method of claim 1, wherein the lyophilized composition is a powder.

4. The method of claim 1, wherein the at least one substantially pharmaceutically inert compound is mannitol.

5. The method of claim 1, wherein the one or more alkali bases is sodium hydroxide or potassium hydroxide.

6. The method of claim 1, wherein the at least one substantially pharmaceutically inert compound is mannitol and the one or more alkali bases comprise sodium hydroxide.

7. The method of claim 1, wherein the lyophilized composition contains said one or more alkali bases in an amount sufficient such that when said lyophilized composition is reconstituted in deionized water at a concentration of about 0.2 mg/mL to about 1.0 mg/mL of the glibenclamide or a pharmaceutically acceptable salt thereof, its pH is greater than 10.

8. The method of claim 1, wherein the lyophilized composition further includes a buffer and a second pharmaceutically active compound.

9. The method of claim 1, wherein glibenclamide is in the form of a pharmaceutically acceptable salt.

10. The method of claim 1, wherein the lyophilized composition contains less than 0.1% w/w of agents that enhance the solubility of glibenclamide.

11. The method of claim 1, wherein said reconstituted pharmaceutical formulation comprises glibenclamide or a pharmaceutically acceptable salt thereof at a concentration of about 1 mg/ml.

12. The method of claim 1, wherein said reconstituted pharmaceutical formulation comprises glibenclamide or a pharmaceutically acceptable salt thereof, mannitol, sodium hydroxide, and water, and has an osmolality of 200 mOsm to 400 mOsm.

13. The method of claim 1, wherein said reconstituted pharmaceutical formulation is suitable for intravenous administration.

14. The method of claim 1, wherein said reconstituted pharmaceutical formulation is suitable for administration as a bolus injection.

15. The method of claim 1, wherein said reconstituted pharmaceutical formulation is suitable for administration as an intravenous infusion.

16. A container containing a reconstituted pharmaceutical formulation comprising a lyophilized composition that comprises:
   a) glibenclamide or a pharmaceutically acceptable salt thereof;
   b) at least one substantially pharmaceutically inert compound selected from the group consisting of glucose, fructose, mannose, galactose, mannitol, sorbitol, lactose, trehalose, sucrose, sodium chloride and potassium chloride; and
   c) one or more alkali bases,
reconstituted in deionized water at a concentration of about 0.2 mg/mL to about 1.0 mg/mL of the glibenclamide or a pharmaceutically acceptable salt thereof, said reconstituted pharmaceutical formulation having a pH greater than 8,
   wherein the lyophilized composition is stable for at least 3 months at 25° C. and 60% relative humidity.

17. The container of claim 16, wherein the at least one substantially pharmaceutically inert compound is mannitol.

18. The container of claim 16, wherein the one or more alkali bases is sodium hydroxide or potassium hydroxide.

19. The container of claim 16, wherein the at least one substantially pharmaceutically inert compound is mannitol and the one or more alkali bases comprise sodium hydroxide.

20. The container of claim 16, wherein glibenclamide is in the form of a pharmaceutically acceptable salt.

21. The container of claim 16, wherein the lyophilized composition contains less than 0.1% w/w of agents that enhance the solubility of glibenclamide.

22. The container of claim 16, wherein said reconstituted pharmaceutical formulation comprises glibenclamide or a pharmaceutically acceptable salt thereof at a concentration of about 1 mg/ml.

23. The container of claim 16, wherein said reconstituted pharmaceutical formulation comprises glibenclamide or a pharmaceutically acceptable salt thereof, mannitol, sodium hydroxide, and water, and has an osmolality of 200 mOsm to 400 mOsm.

* * * * *